United States Patent
Kapur

(10) Patent No.: US 11,738,131 B2
(45) Date of Patent: *Aug. 29, 2023

(54) EXPANDABLE ECMO EXTENSION CANNULA SYSTEM

(71) Applicant: Tufts Medical Center, Inc., Boston, MA (US)

(72) Inventor: Navin K. Kapur, Hanover, MA (US)

(73) Assignee: Tufts Medical Center, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/151,982

(22) Filed: Jan. 9, 2023

(65) Prior Publication Data

US 2023/0158223 A1    May 25, 2023

Related U.S. Application Data

(63) Continuation-in-part of application No. 17/663,205, filed on May 12, 2022, now Pat. No. 11,547,786, which is a continuation-in-part of application No. PCT/US2021/025461, filed on Apr. 1, 2021, which is (Continued)

(51) Int. Cl.
  *A61M 1/36* (2006.01)
  *A61M 25/00* (2006.01)

(52) U.S. Cl.
  CPC ........ *A61M 1/3613* (2014.02); *A61M 1/3659* (2014.02); *A61M 2025/0024* (2013.01); *A61M 2210/127* (2013.01)

(58) Field of Classification Search
  CPC .............. A61M 1/3659; A61M 1/3613; A61M 25/0012; A61M 39/06; A61M 2025/0024; A61M 2210/127; A61M 2039/0633
  See application file for complete search history.

(56) References Cited

U.S. PATENT DOCUMENTS

| | | |
|---|---|---|
| 5,125,903 A | 6/1992 | McLaughlin et al. |
| 5,195,980 A | 3/1993 | Catlin |
| 5,269,764 A | 12/1993 | Vetter et al. |

(Continued)

OTHER PUBLICATIONS

U.S. Appl. No. 16/840,284 / U.S. Pat. No. 11,331,421, filed Apr. 3, 2020 / May 17, 2022.

(Continued)

*Primary Examiner* — Emily L Schmidt
(74) *Attorney, Agent, or Firm* — Eversheds Sutherland (US) LLP; Christopher C. Bolten; Albert K. Heng

(57) ABSTRACT

An extension cannula for use with a conventional ECMO return cannula is provided. The extension cannula includes a flexible conduit transitionable between a collapsed insertion state and an expanded deployed state when in communication with blood flow from an ECMO machine via the ECMO return cannula. The extension cannula may be positioned through a conventional ECMO return cannula such that the proximal end of the flexible conduit is disposed within and proximal to the end of the ECMO return cannula, while the distal end of the flexible conduit is disposed in a patient's thoracic aorta to deliver oxygenated blood directly to the patient's thoracic aorta via one or more pores at the distal region of the flexible conduit to improve cerebral oxygenation, maintain systemic arterial pulsatility, and reduce the potential for end-organ injury.

18 Claims, 32 Drawing Sheets

Related U.S. Application Data a continuation-in-part of application No. 16/840,284, filed on Apr. 3, 2020, now Pat. No. 11,331,421.

(56) References Cited

U.S. PATENT DOCUMENTS

| | | | |
|---|---|---|---|
| 6,083,198 | A | 7/2000 | Afzal |
| 6,183,443 | B1 | 2/2001 | Kratoska et al. |
| 6,210,365 | B1 | 4/2001 | Afzal |
| 6,241,666 | B1 | 6/2001 | Pomeranz et al. |
| 6,632,236 | B2 | 10/2003 | Hogendijk |
| 7,938,809 | B2 | 5/2011 | Lampropoulos et al. |
| 8,996,095 | B2 | 3/2015 | Anderson et al. |
| 9,144,662 | B2 | 9/2015 | Di Caprio et al. |
| 10,485,956 | B2 | 11/2019 | O'Donovan |
| 11,331,421 | B2 | 5/2022 | Kapur |
| 2006/0079859 | A1 | 4/2006 | Elkins et al. |
| 2011/0190683 | A1* | 8/2011 | Gellman ............ A61M 25/0023 606/191 |
| 2013/0274783 | A1 | 10/2013 | Wynberg |
| 2014/0012281 | A1 | 1/2014 | Wang et al. |
| 2014/0221964 | A1 | 8/2014 | Xiao et al. |
| 2016/0158489 | A1 | 6/2016 | Wu et al. |
| 2017/0080178 | A1 | 3/2017 | O'Connell et al. |
| 2017/0238951 | A1 | 8/2017 | Yang et al. |
| 2018/0193026 | A1 | 7/2018 | Yang et al. |
| 2018/0207399 | A1 | 7/2018 | Chou et al. |
| 2018/0243004 | A1 | 8/2018 | Von Segesser |
| 2019/0160259 | A1 | 5/2019 | Cottone et al. |
| 2019/0247564 | A1 | 8/2019 | Lu et al. |
| 2019/0358434 | A1 | 11/2019 | Fuller et al. |
| 2020/0146852 | A1 | 5/2020 | Raychev et al. |
| 2021/0308359 | A1 | 10/2021 | Kapur |
| 2022/0280709 | A1 | 9/2022 | Kapur |

OTHER PUBLICATIONS

U.S. Appl. No. 17/663,205 / U.S. Pat. No. 11,547,786, filed May 12, 2022 / Jan. 10, 2023.

International Search Report & Written Opinion dated Sep. 13, 2021 in Int'l PCT Patent Appl. Serial No. PCT/US2021/025461.

Pavlushkov, et al, Cannulation Techniques for Extracorporeal life Support, Review Article on Extracorporeal Life Support, Annals of Translational Medicine, 5(4):70 (Feb. 2017).

Sulimov, M.D., et al., Rescue Peripheral Intervention Using a Peripheral ECMO-Cannula as Vascular Access, J. Amm. Golf. Cardial. Intv., Jan. 2020. 29, epublished 001:10.1 016/j.jcin.2019.11.038.

Swain, et al., Transvalvular Ventricular Unloading Before Reperfusion in Acute Myocardial Infarction, Journal of the American College of Cardiology, 76(6):685-699 (Aug. 2020).

Wickramarachchi, et al., The Effect of Arterial Cannula Tip Position on Differential Hypoxemia During Venoarterial Extracorporeal Membrane Oxygenation, Physical and Engineering Sciences in Medicine, https://doi.org/10.1007/s13246-022-01203-6, published online: Dec. 2, 2022.

* cited by examiner

120 ↘

121
Insert distal end of extension cannula into patient, the proximal end of the extension cannula coupled to an ECMO cannula, and at least a portion of the extension cannula disposed within a peel away introducer 122
Position the introducer through the skin such that the distal end of extension cannula is positioned within the artery 123
Retract and peel away introducer from extension cannula 124
Position distal end of extension cannula within thoracic aorta 125
Perfuse oxygenated blood from the ECMO cannula through the extension cannula to the thoracic aorta 126
Turn off ECMO machine to return extension cannula to collapsed insertion state 127
Remove the extension cannula and the ECMO cannula from the patient

FIG. 12

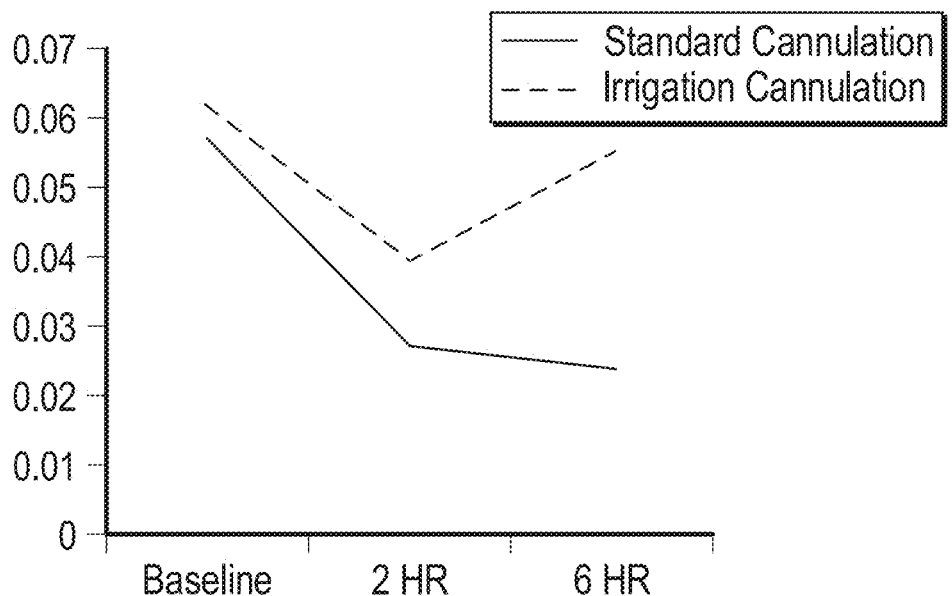
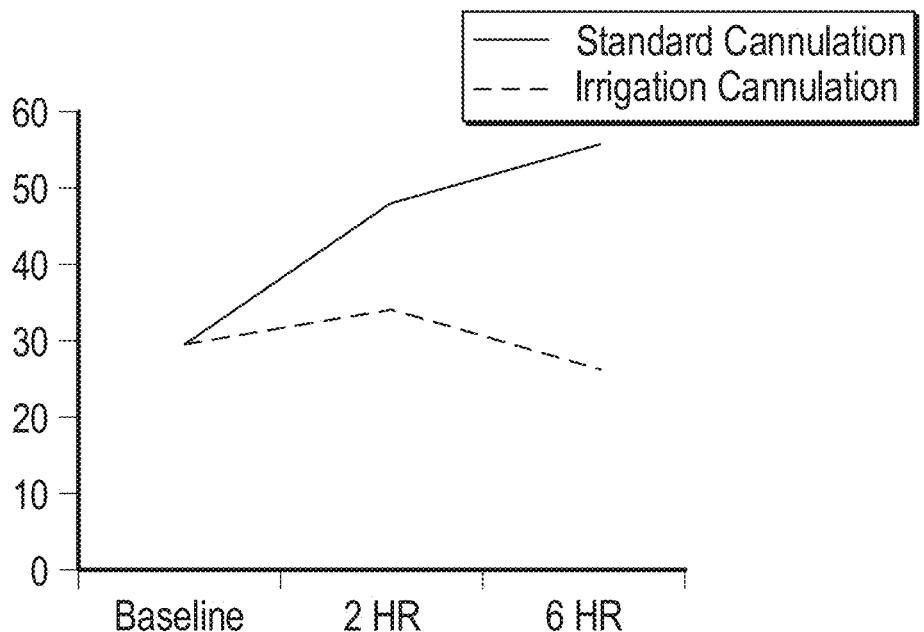
FIG. 22

EXPANDABLE ECMO EXTENSION CANNULA SYSTEM

CROSS-REFERENCE TO RELATED APPLICATIONS

This application is a continuation-in-part application of U.S. patent application Ser. No. 17/663,205, filed May 12, 2022, now U.S. Pat. No. 11,547,786, which is a continuation-in-part application of International PCT Patent Application Serial No. PCT/US2021/025461, filed Apr. 1, 2021, which is a continuation-in-part application of U.S. patent application Ser. No. 16/840,284, filed Apr. 3, 2020, now U.S. Pat. No. 11,331,421, the entire contents of each of which are incorporated herein by reference.

FIELD OF THE INVENTION

This application relates generally to systems and methods for improving systemic perfusion and reducing complications during venous-arterial extracorporeal membrane oxygenation (VA-ECMO), and more specifically, for improving perfusion using an in-line connector and an extension cannula to deliver oxygenated blood directly to the thoracic aorta.

BACKGROUND

Nearly 23 million people suffer from heart failure (HF) worldwide, which affects approximately 7 million individuals in the United States with healthcare expenditures reaching nearly 40 billion dollars per year. Acute myocardial infarction (AMI) is a leading cause of HF and occurs in over 650,000 individuals per year in the United States. Despite early revascularization in AMI, for every 5% increase in infarct size, one-year mortality and HF hospitalization are increased by 20%. Paradoxically, coronary reperfusion may accelerate myocardial injury and cardiomyocyte death in AMI. Despite improvements in reperfusion time, subsequent HF remains a significant problem and new approaches are needed to reduce myocardial damage in AMI.

Arterial perfusion to every major organ system, including the heart, kidneys and brain, is determined by arterial pressure, blood flow, vascular tone, and intra-organ vascular resistance. When a patient experiences low arterial perfusion due to heart failure, cardiopulmonary failure, and cardiogenic or septic shock, venous-arterial extracorporeal membrane oxygenation (VA-ECMO) systems may be used to provide both circulatory and gas exchange support by augmenting the flow of oxygenated blood. See, e.g., Pavlushkov E, Berman M, Valchanov K. Cannulation techniques for extracorporeal life support. Ann Transl Med 2017; 5(4):70. doi: 10.21037/atm.2016.11.47. Specifically, VA-ECMO drains blood from the venous system, oxygenates this blood outside of the patient, and then delivers oxygenated blood back to the arterial system, e.g., via the femoral artery. VA-ECMO is most commonly performed via large-bore cannulas placed in the femoral vein and femoral artery (known as peripheral VA-ECMO). VA-ECMO is an established strategy for cardiopulmonary support. Large-bore ECMO cannulae for use in adult humans generally range in diameter from 15 Fr (5.0 mm) to 25 Fr (8.3 mm) and are used to deliver life-sustaining blood flow rates of between 3 and 8 liter/min.

Despite increasing utilization of VA-ECMO, with nearly 5,000 extracorporeal membrane oxygenation devices in use annually in the U.S. alone, in-hospital mortality remains around 60%. One explanation for these poor outcomes is that peripherally cannulated VA-ECMO may cause kidney injury, increase the risk of stroke, and promote cerebral ischemia, bleeding, and vascular injury. Further, more than one large-bore cannula may be required to achieve high flow rates needed for systemic perfusion with VA-ECMO. Cannula number and size are directly associated with increased risk of bleeding, vascular trauma, and acute limb ischemia. Finally, peripherally cannulated VA-ECMO may pressurize the entire aorta and increase pressure inside the heart, which increases ventricular wall stress and myocardial oxygen consumption, thereby expanding myocardial damage or infarct size in the setting of a heart attack and increasing fluid in the lungs thereby causing acute lung injury. Recent data also shows that VA-ECMO may cause damage to mitochondria located within the heart, which may limit myocardial recovery. To mitigate heart or lung injury, concomitant devices such as intra-aortic balloon pumps and Impella® pumps (made available by AbioMed, Danvers, Mass.) may be used concomitantly with VA-ECMO and require additional vascular puncture. All of these complications are associated with increased mortality, long-term morbidity, length of stay in the hospital, and healthcare costs. New approaches to limit complications associated with VA-ECMO are required.

Studies indicate that VA-ECMO support may decrease kidney function and even cause acute kidney injury due to increased arterial pressure and loss of pulsatile flow to the kidney resulting from the high rates of blood flow localized to the outlet region of arterial outlet return cannulas with conventional VA-ECMO. Such injuries may in turn activate autoregulatory mechanisms of the kidneys. For example, high rates of non-pulsatile flow encountered with conventional VA-ECMO cannulas have been observed to increase vascular resistance, which in turn increases the workload of the kidneys and exacerbates oxygen consumption. Up to 70% of patients receiving VA-ECMO develop acute kidney injury, which is directly associated with mortality. Studies have further indicated that use of VA-E may lead to a significant increase in arterial flow, as well as promote an increase in pressure within the organ itself, which in turn decreases flow in the renal vein. Thus, the net effect of VA-ECMO use, with conventional return cannulas, is an increase in pressure inside the organ, such that flow through the kidney is decreased. These physiological findings correlate with an increase in biomarkers of kidney injury, suggesting that one mechanism responsible for kidney injury may be related to pressure build-up inside the kidney and a net decrease of blood flow through the kidney.

Previously known efforts to reduce perfusion injury are known in the art. For example, U.S. Pat. No. 6,083,198 to Afzal describes a perfusion catheter having segmented flow regions, in which an arterial return catheter includes a series of apertures along its length to more evenly distribute blood within the aorta, including the aortic arch. One drawback of the system described in that patent, however, is that the inner catheter includes a reduced diameter than the outer catheter, thereby reducing flow rates to the distal-most portions of the catheter.

Recent studies also indicate that VA-ECMO use results in increased risk of stroke, e.g., acute ischemic stroke and hemorrhagic stroke. Because VA-ECMO induces retrograde blood flow in the femoral artery towards the aorta, the brain is the last major organ to receive oxygenated blood delivered via a conventional femoral artery cannula. Further, in patients exhibiting north-south syndrome, e.g., when compromised lung function results in ejection of deoxygenated blood from the left ventricle into the ascending aorta, differential hypoxia may occur as a result of VA-ECMO patients' dependence on retrograde flow to deliver oxygenated blood to the upper body. To mitigate this effect, physicians currently perform additional vascular punctures in the arteries or veins to place additional large-bore cannulas that increase the risk of complications.

Central VA-ECMO, in which oxygenated blood is delivered directly to a central location, e.g., via a surgical cut-down to the aortic arch, has been hypothesized to provide more oxygenated blood flow to the brain and thus reduce the risk of stroke. However, such cannulation, as described for example in U.S. Pat. No. 6,210,365 to Afzal, requires invasive surgery and involves additional potential complications. Another solution theorized would be to deliver oxygenated blood directly to the venous side of the patient via an ECMO cannula; however, this would require creating additional large-bore punctures in the patient's vasculature and may be further complicated by the already existing cannula residing in the venous circulation from the original VA-ECMO configuration. Additionally, placement of rigid cannulas from the peripheral artery into a central location in the thoracic aorta may be limited by the inability to navigate large bore cannulas through the iliofemoral bifurcation, tortuous aortas, or across calcified aortas with atheromatous material lining the aorta.

In view of the foregoing, it would be desirable to provide systems and methods for delivering oxygenated blood via VA-ECMO from a point of entry in the femoral artery to a more central location to the patient, e.g., the thoracic aorta, to supply oxygenated blood to the brain and induce antegrade flow to lower portions of the descending aorta. Such systems and methods may thus improve blood flow to the brain, preserve brain function, reduce the risk of ischemic stroke, and reduce blood flow rates and pressures that could induce kidney injury.

U.S. Pat. No. 8,996,095 to Anderson describes a coronary guide extension catheter having a push member and a distal tubular member, which is configured to be positioned in a coronary artery for use during percutaneous transluminal coronary angioplasty. The guide extension catheter described in that patent is designed to stabilize the distal end of a coronary guide catheter to prevent movement away from the patient's ostium due to beating of the heart during the interventional procedure. Similarly, U.S. Pat. No. 10,485,956 to O'Donovan describes a guide extension catheter having a groove in a push member and a distal shaft for guiding an interventional coronary device therethrough. Such coronary guide extension catheters are unsuitable for use as perfusion cannulas in VA-ECMO due to the small lumen diameters and resulting low blood flow rates that could be achieved. Guide extension catheters typically have a fixed diameter of between 6 Fr (2 mm) and 8 Fr (2.7 mm). These coronary guide extension catheters are not meant to redirect blood flow, but rather to facilitate delivery of coronary equipment into distal portions of the coronary vasculature.

U.S. Pat. No. 6,632,236 to Hogendijk describes a self-expanding catheter for use in stent delivery, in which a catheter is transluminally inserted in a collapsed delivery state, and self-expands to an expanded deployed state upon removal of a delivery sheath. That patent describes a self-expanding anchor formed of a self-expanding wire weave having an elastomeric polymeric coating, and is configured to protect against embolization during vascular interventions. The concept described in Hogendijk is not meant to redirect blood flow, but rather to filter out elements in the blood stream. Similarly, U.S. Pat. No. 6,183,443 to Kratoska describes an expandable introducer sheath for percutaneously introducing intravascular angioplasty catheters. Such self-expanding catheters have not been contemplated for use with VA-ECMO systems for perfusing oxygenated blood.

In view of the disadvantages of the previously known ECMO perfusion catheters, it would be desirable to provide a device for use with an ECMO system that can enhance blood flow to the thoracic aorta and aortic arch, improve cerebral oxygenation, maintain systemic arterial pulsatility, and reduce the potential for perfusion injury to the kidneys using a single port of access, thereby avoiding bleeding and vascular injury associated with contemporary VA-ECMO.

It further would be desirable to provide a device for use with an ECMO system that avoids the small flow lumen sizes of previously known reperfusion catheters, thereby permitting enhanced blood flow rates to the ascending aorta and aortic arch, while maintaining or reducing the diameter of the vascular opening to the femoral artery required to introduce the return cannula.

In contemporary practice, VA-ECMO is also used to support commonly performed life-saving procedures such as coronary angioplasty, aortic valvuloplasty, or aortic valve replacement. However, a major limitation of these approaches is the need for additional vascular access to place vascular sheaths and/or catheters for required interventional equipment in addition to the existing VA-ECMO circuit. This can be prohibitive for patients who have peripheral vascular disease, concomitant vascular injury, or vessels occupied by other life-saving equipment. Further, under emergent conditions, placing additional vascular access can be challenging and increase risk of injury.

U.S. Pat. Nos. 5,125,903, 5,195,980, 5,269,764, 7,938,809 describe percutaneous catheter introducers/connectors having hemostatic valves for permitting passage of elongated interventional devices into a patient's vasculature, and a side port for connection with, e.g., an outside source of perfusion, aspiration, contrast media, medicaments, etc. These systems are not designed for use with VA-ECMO. Moreover, no existing approach allows for simple and effective access to the VA-ECMO circuit for delivery of additional interventional equipment. Current Y-connectors used to provide access to an ECMO circuit suffer from numerous disadvantages including reduction in the effective lumen of the ECMO return cannula creating an undesirable pressure gradient, difficult angulations requirements that prohibit introduction of additional catheters without risk of kinking or catheter disruption. Such previously known connectors require the introducer sheath to be inserted nearly 25 to 30 cm more distal than usual due to interposition connecting tubing, thereby limiting access to the thoracic aorta, aortic root, aortic valve or coronary vasculature for therapeutic interventions. Such connectors also pose a risk of bleeding during ECMO disconnection and reconnection, with increased risk of air embolism and contamination due to disconnection from the ECMO circuit. See, e.g., Dmitriy S. Sulimov, M D et al., "Rescue Peripheral Intervention Using a Peripheral ECMO-Cannula as Vascular Access," J Am Coll Cardiol Intv. 2020 Jan. 29. Epublished DOI: 10.1016/j.jcin.2019.11.038.

It would therefore be desirable to provide a connector for providing simple and effective access to an ECMO circuit for delivery of interventional equipment.

SUMMARY OF THE INVENTION

In accordance with the principles of the present invention, devices and methods are provided for use with ECMO systems that overcome the disadvantages of the previously known ECMO reperfusion catheters. Specifically, devices constructed in accordance with the present invention enhance blood flow to the thoracic aorta, improve cerebral oxygenation, maintain systemic arterial pulsatility, and reduce the potential for end-organ injury.

In accordance with one aspect of the present invention, a kit for use with an ECMO machine is provided. The kit may include a cannula comprising a proximal region having an inlet configured to be coupled to the ECMO machine, and an outlet configured to be disposed at a location within a patient's vasculature proximal of a patient's renal vessels, and an extension cannula. The extension cannula may include a flexible conduit having a proximal end, a distal end, a length extending therebetween, and a lumen in an expanded deployed state. The flexible conduit may transition from a collapsed insertion state to the expanded deployed state when in communication with a blood flow from the ECMO machine so that the lumen forms a continuation of a blood flow path through the cannula. The extension cannula further may include an elongated shaft having a distal region coupled to the distal end of the flexible conduit. The elongated shaft may be configured to advance the flexible conduit in the collapsed insertion state to locate the distal end beyond the patient's renal vessels. The kit further may include a peel-away introducer disposed on at least a portion of the flexible conduit. The peel-away introducer may be retracted proximally relative to the flexible conduit and peeled off of the flexible conduit. Moreover, the length of the flexible conduit may be selected so that when the proximal end is located within the outlet at the location within the patient's vasculature proximal of the patient's renal vessels, the distal end extends beyond the patient's renal vessels.

The peel-away introducer may have a diameter that is at most equal to a diameter of the cannula. In some embodiments, the peel-away introducer may extend along an entire length of the flexible conduit. The elongated shaft may extend from the distal end of the flexible conduit proximally along a lateral side of the flexible conduit. For example, the elongated shaft may extend along the inner surface of the flexible conduit, along the outer surface of the flexible conduit, or may be embedded within the membrane of the flexible conduit. Alternatively, the elongated shaft may extend from the distal end of the flexible conduit proximally within the lumen along a longitudinal axis of the flexible conduit. For example, the elongated shaft may extend along a center portion of the lumen. The elongated shaft may be configured so that the blood flow path does not pass through the elongated shaft. Moreover, the elongated shaft may contain a hypotube which provides a lumen configured to receive a guidewire therethrough.

The extension cannula further may include a support coupled to a distal region of the flexible conduit. The support may extend circumferentially along the flexible conduit and may transition from a collapsed delivery state to an expanded deployed state. In addition, the extension cannula may include a plurality of connection structures extending between the distal end of the flexible conduit and the support. The plurality of connection structures may transition from a collapsed delivery state to an expanded deployed state. A distal end of the elongated shaft may include an atraumatic tip configured to be coupled to the support via the plurality of connection structures. The flexible conduit may include at least one of polyethylene, polyurethane, or nylon. Further, an outlet of the flexible conduit may include one or more pores disposed at a distal region of the flexible conduit. The proximal end of the flexible conduit may be fixedly coupled to the cannula within the outlet of the cannula.

The kit further may include one or more sensors disposed at a distal region of the extension cannula. The one or more sensors may be configured to measure at least one of pressure, flow, or oxygen saturation within the patient's vasculature. Accordingly, the kit further may include a console operatively coupled to the one or more sensors, the console configured to display measurements of the one or more sensors. Moreover, the elongated shaft may have a lumen sized and shaped to receive one or more electrical wires extending between the one or more sensors and the console.

In accordance with another aspect of the present invention, a method for improving systemic perfusion is provided. The method may include: advancing a distal end of a flexible extension cannula within a patient's vasculature via an elongated shaft coupled to the distal end of the flexible extension cannula, a proximal region of the flexible extension cannula coupled to an outlet of an ECMO return cannula in fluid communication with an ECMO machine, at least a portion of the flexible extension cannula disposed within a peel-away introducer; positioning the peel-away introducer into the patient's vasculature, such that a proximal end of the peel-away introducer remains external to the patient and the distal end of the flexible extension cannula is positioned within the patient's vasculature; retracting the peel-away introducer relative to the flexible extension cannula and peeling the peel-away introducer off of the flexible extension cannula; advancing the ECMO return cannula into the patient's vasculature such that the flexible extension cannula extends from a location proximal to the patient's renal vessels to a location beyond the patient's renal vessels; transitioning the flexible extension cannula from a collapsed insertion state to an expanded deployed state when in communication with a blood flow from the ECMO machine, the flexible extension cannula comprising a lumen in the expanded state; and delivering the blood flow through the lumen of the flexible extension cannula to the location beyond the patient's renal vessels via a plurality of pores disposed at a distal region of the flexible extension cannula to thereby improve systemic perfusion. Transitioning the flexible extension cannula from the collapsed insertion state to the expanded deployed state may include transitioning a support extending circumferentially along a distal region of the flexible extension cannula from a collapsed delivery state to an expanded deployed state, and optionally, transitioning a plurality of connection structures extending from the distal end of the flexible extension cannula to the support from a collapsed delivery state to an expanded deployed state.

BRIEF DESCRIPTION OF THE DRAWINGS

FIG. 12 is a flow chart of exemplary steps for improving perfusion during ECMO using the extension cannula of FIGS. 11A to 11C in accordance with the principles of the present invention.

FIG. 22 are graphs illustrating renal arterial pulsatility and renal arterial microvascular resistance for standard conventional ECMO cannulation and an exemplary alternate cannulation system of the present invention.

DETAILED DESCRIPTION OF THE INVENTION

Systems and methods are provided for use with ECMO systems to enhance blood flow to the thoracic aorta, ascending aorta and aortic arch, thereby facilitating normal antegrade flow to the carotid and other downstream arteries, while reducing high blood flow rates and the potential for reperfusion injury to the kidneys. The systems and methods of the present invention also may ameliorate the occurrence of north-south syndrome in patients with impaired lung function, thereby ensuring adequate flow of oxygenated blood to the patient's cerebral vasculature.

Figure 1A:
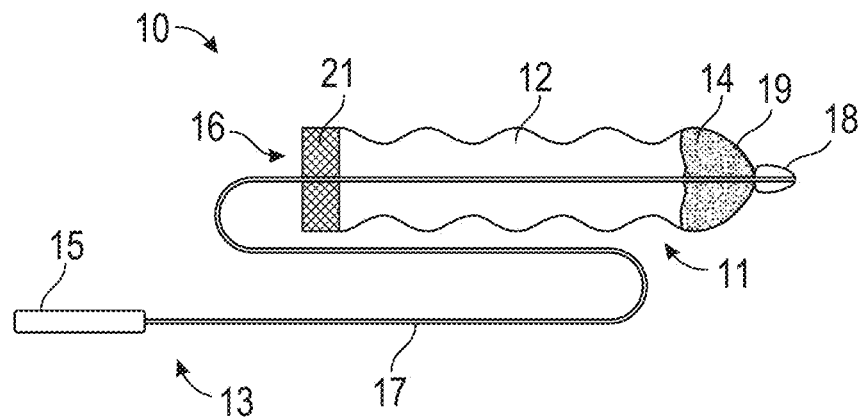
FIG. 1A is a side view of an exemplary extension cannula for improving reperfusion during ECMO, constructed in accordance with the principles of the present invention, with the extension conduit in a partially collapsed state.
Figure 1B:
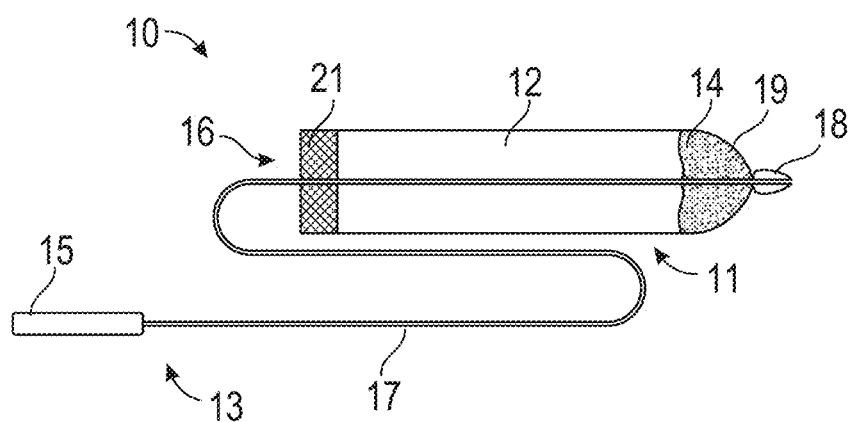
FIG. 1B is a side view of extension cannula of FIG. 1A in an expanded state.

Referring now to FIGS. 1A and 1B, an exemplary extension cannula suitable for use with a conventional VA-ECMO cannula is described. Extension cannula 10 may be constructed as described in U.S. Patent Appl. Pub. No. 2022/0280709, the entire contents of which is incorporated herein by reference. For example, extension cannula 10 may include elongated shaft 17, e.g., a hypotube, extending between distal region 11 and proximal region 13 of extension cannula 10. Hypotube 17 is formed of a material, e.g., stainless steel rod, having sufficient rigidity to permit extension cannula 10 to be advanced through a conventional ECMO reperfusion cannula so that distal region 11 of expandable conduit 12 may be disposed with its outlet extending beyond a patient's renal arteries, and preferably extending in a patient's ascending aorta or in the vicinity of the aortic arch. For example, hypotube 17 may have a lumen sized and shaped to receive a guidewire therethrough, such that extension cannula 10 may be advanced through the conventional ECMO reperfusion cannula to the target location over a guidewire via the lumen of hypotube 17. Extension cannula 10 optionally may include handle 15 coupled to hypotube 17 at proximal region 13 of extension cannula 10 for maneuvering extension cannula 10.

The distal end of hypotube 17 may include atraumatic tip 18, which may be coupled to the distal region of expandable conduit 12 via connection structure 19, e.g., one or more umbrella-like struts. Connection structure 19 may be self-expandable between a collapsed delivery state and an expanded deployed state, e.g., upon exposure from sheath 40. As shown in FIGS. 1A and 1B, connection structure 19 may have a curved shape in the expanded deployed state. Connection structure 19 may be embedded within the biocompatible material forming expanding conduit 12. Additionally or alternatively, connection structure 19 may be coupled to the inner surface of expandable conduit 12 or to the outer surface of expandable conduit 12, or both. Hypotube 17 does not form part of the blood flow path through the lumen of expandable conduit 12. In one embodiment, connection structure 19 is not self-expandable, such that connection structure 19 transitions from the collapsed delivery state to the expanded deployed state when blood flows through the lumen of expandable conduit 12, thereby causing expandable conduit 12 to fill with blood.

Expandable conduit 12 is made of a soft flexible material, such as polyethylene, polyurethane, or nylon, and may include pores 14 at its distal region that permit blood to perfuse through the material as the flow is directed through the lumen of expandable conduit 12. For example, expandable conduit 12 has inlet 16 at its proximal end and an outlet, e.g., plurality of pores 14, at its distal region, and a lumen extending therethrough for permitting blood flow. Pores 14 may be sized and shaped such that, as blood flows from the ECMO machine and through the conventional ECMO reperfusion cannula and the lumen of expandable conduit 12, the blood flow exits expandable conduit 12 via pores 14, while causing expandable conduit 12 to fill with blood and transition from a collapsed delivery state, as shown in FIG. 1A, to the expanded deployed state, as shown in FIG. 1B. Moreover, expandable conduit 12 has a length sufficient to extend from the outlet of the conventional ECMO reperfusion cannula to a position above the patient's renal arteries, and more preferably, into the thoracic aorta, e.g., 15-120 cm, or preferably 20-80 cm or 30-50 cm. Notably, the lightweight sock-like structure provides advantages including, for example, ease of deployment through tortuous or diseased aortas, as well as no impingement on the spinal cord as most patients are lying flat such that use of a rigid cannula may impinge on the spinal cord.

In addition, expandable conduit 12 may include a self-expanding support structure, e.g., anchoring stent 21, such as a mesh, weave or braid formed of a shape-memory metal or stainless steel, at its proximal end such that anchoring stent 21 may transition from a collapsed insertion state and an expanded deployed state within the lumen of the conventional ECMO reperfusion cannula to thereby anchor expandable conduit 12 within the conventional ECMO reperfusion cannula. For example, anchoring stent 21 may be biased toward the expandable deployed state, such that anchoring stent 21 may self-expand upon exposure from sheath 40. Anchoring stent 21 may be covered by a flexible and biocompatible covering, or alternatively, anchoring stent 21 may be uncovered. Anchoring stent 21 may be formed of a stainless steel mesh, weave or braid having a preset expanded diameter that forms a central lumen, such that expandable conduit 12 may be contracted when pulled within smaller diameter delivery sheath 40. Alternatively, anchoring stent 21 may be a mesh, weave or braid formed of a shape-memory metal such as a nickel-titanium alloy ("Nitinol"), and having a predetermined expanded diameter that forms the internal lumen. In this way, expandable conduit 12 may be contracted to the collapsed insertion state when pulled within delivery sheath 40 as described in further detail below.

In the fully expanded deployed state, anchoring stent 21 assumes a diameter substantially the same as, or even larger than, the internal lumen of a conventional VA-ECMO cannula. For example, the lumen of anchoring stent 21 may be at least 15 Fr in the expanded state. Accordingly, when deployed within the lumen of the conventional ECMO cannula, anchoring stent 21 will expand to the diameter of the lumen of the conventional ECMO cannula, such that anchoring stent 21 will apply a radially outward force against the inner surface of the conventional ECMO cannula to thereby anchor anchoring stent 21 within the lumen of the conventional ECMO cannula. When inserted through a conventional ECMO cannula and anchored to the conventional ECMO cannula via anchoring stent 21, expandable conduit 12 permits enhanced blood flow to the ascending aorta and aortic arch, while maintaining the diameter of the vascular opening in the femoral artery required to introduce the conventional VA-ECMO return cannula. In some embodiments, the biocompatible polymer coating may include additional pores proximal to pores 14 that permit blood to perfuse laterally through the material, thereby reducing jetting from pores 14. Like self-expanding conduit 12, expandable conduit 12 may include one or more radiopaque markers disposed along the distal end of expandable conduit 12 adjacent pores 14 to permit its location to be determined fluoroscopically.

In some embodiments, inlet 16 at the proximal end of expandable conduit 12 may have a feature for facilitating recapture of expandable conduit 12 within the delivery sheath. For example, expandable conduit 12 may have a plurality of angled legs that couple anchoring stent 21 of expandable conduit 12 to shaft 17 to facilitate resheathing of expandable conduit 12 for removal. Preferably, the angled legs are flexible and of uniform length, so that when the distal end of sheath 40 is advanced over the angled legs, the legs flex inward to cause anchoring stent 21 to collapse inward toward its collapsed delivery state. Alternatively, when expandable conduit 12 does not have a feature for facilitating recapture of expandable conduit 12, expandable conduit 12 may be removed along with the conventional ECMO cannula by turning off the ECMO machine to stop blood flow into expandable conduit 12, thereby causing expandable conduit 12 to return to a semi-collapsed state. Accordingly, expandable conduit 12 and the conventional ECMO cannula may be removed together from the patient's vasculature.

In some embodiments, sheath 40 may have a rapid exchange configuration, with sheath 40 having a length suitable for covering the entire length of expandable conduit 12 but is joined to a support shaft and a handle coupled to the end of the support shaft. In this manner, sheath 40 may be back-loaded over the proximal end of shaft 17 of extension cannula 10 and manipulated using the support shaft via the handle, without interfering with the ability to manipulate the proximal end of shaft 17.

Figure 2A:
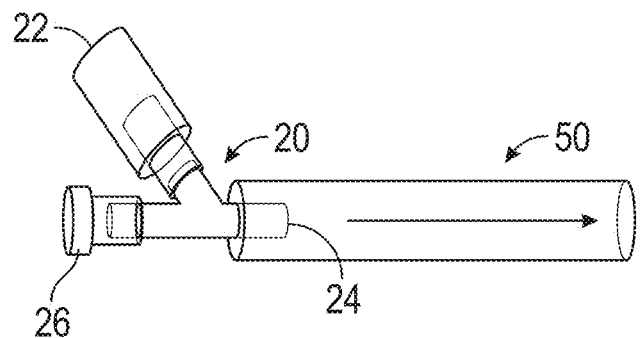
FIGS. 2A-2C are schematic views illustrating use of an exemplary in-line connector with the extension cannula of FIGS. 1A and 1B in an ECMO system.
Figure 2B:
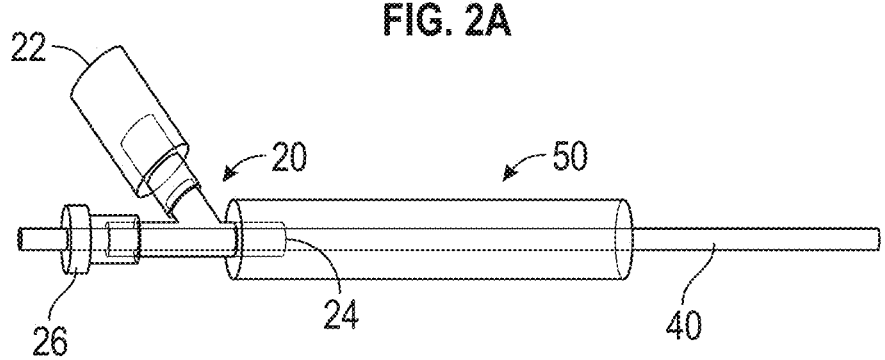
Figure 2C:
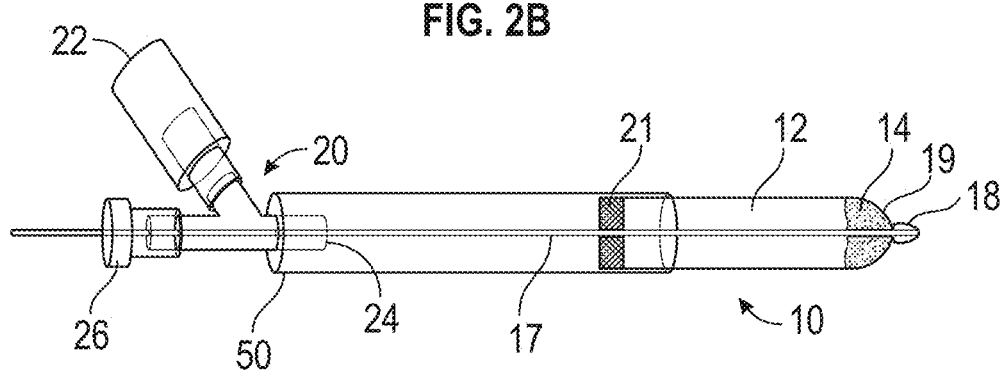

Referring now to FIGS. 2A to 2C, operation of the embodiment of the extension cannula of FIGS. 1A and 1B is schematically depicted in conjunction with an optional in-line connector 20, as described in U.S. Pat. No. 11,331,421, the entire contents of which are incorporated by reference. For example, in-line connector 20 has first branch inlet 22 configured to be coupled to an outlet of a conventional ECMO machine for receiving oxygenated blood from an ECMO circuit, second branch inlet 26 having a hemostatic valve welded therein, and outlet 24 configured to be coupled to a conventional ECMO cannula. First branch inlet 22 and second branch inlet 26 each are in fluid communication with outlet 24, and each may include an optional hemostatic valve 25. The fluid pathway extending between first branch inlet 22 and outlet 24 thus permits oxygenated blood received from an ECMO circuit to flow to through the conventional ECMO cannula and self-expanding conduit 12. Moreover, the fluid pathway extending between second branch inlet 26 and outlet 24 is sized and shaped to permit delivery therethrough of self-expanding conduit 12 in a collapsed insertion state, e.g., when disposed within delivery sheath 40.

Conventional ECMO cannula 50 may be coupled to outlet 24 of in-line connector 20 and inserted into a patient's arterial vasculature, e.g., via a cut down to the femoral artery, as shown in FIG. 2A. The outlet line from an ECMO machine may be coupled to first branch inlet 22. As shown in FIG. 2B, extension cannula 10, disposed with expandable conduit 12 in its collapsed insertion state within delivery sheath 40, is advanced through the hemostatic valve of second branch inlet 26 of in-line connector 20. Extension cannula 10 is positioned so that the distal end of expandable conduit 12 is disposed in the desired location, e.g., within the thoracic aorta, and the proximal end of expandable conduit 12 lies near the distal outlet of the conventional ECMO reperfusion cannula, e.g., as may be determined under fluoroscopy using, e.g., radiopaque marker bands disposed on sheath 40.

The lumen of sheath 40 preferably is dimensioned to accept and retain expandable conduit 12 in its collapsed insertion state. Sheath 40 is slidably disposed over expandable conduit 12, and accordingly anchoring stent 21 and connection structure 19, so that sheath 40 may be retracted relative to expandable conduit 12, thereby permitting connection structure 19 and/or anchoring stent 21 to transition from the collapsed delivery state to the expanded deployed state upon exposure from sheath 40.

Referring now to FIG. 2C, when sheath 40 and expandable conduit 12 are positioned in the desired location as described above, sheath 40 is retracted while expandable conduit 12 is held in position by hypotube 17 and handle 15, thereby permitting connection structure 19 and/or anchoring stent 21 to transition to their expanded, deployed states. As shown in FIG. 2C, in its expanded deployed state, anchoring stent 21 abuts the inner surface of conventional ECMO reperfusion cannula 50 to thereby anchor expandable conduit 12 within conventional ECMO reperfusion cannula 50. Initially, upon retraction of sheath 40 and expansion of connection structure 19 and/or anchoring stent 21, the portion of expandable conduit 12 between connection structure 19 and anchoring stent 21 may still be in a semi-collapsed delivery state, as shown in FIG. 1A. Expandable conduit 12 may fully transition to its expanded deployed state when in fluid communication with blood flow from the ECMO machine through conventional ECMO reperfusion cannula 50, as shown in FIG. 1B. For example, in a fully expanded state, expandable conduit 12 may have a diameter of 10-20 mm.

Referring again to FIG. 2C, because most of the length of expandable conduit 12 extends past the distal end of conventional ECMO reperfusion cannula 50, oxygenated blood from the ECMO machine may be delivered, e.g., via pores 14, to regions beyond those accessible with a conventional ECMO return cannula. In one preferred embodiment of extension cannula 10, expandable conduit 12 has a length between 15 to 120 cm or preferably, 20-80 cm or longer. In this manner, blood may be delivered in the vicinity of a patient's thoracic aorta, above the patient's renal artery ostia, to avoid high flow rates in the vicinity of the patient's renal arteries and reduce the risk of perfusion injury. In addition, if the distal end of expandable conduit 12 is disposed in the ascending aorta, as may be determined under fluoroscopy using radiopaque marker bands disposed on expandable conduit 12, outflow from pores 14 of expandable conduit 12 can provide oxygenated blood to the cardiac arteries in the vicinity of the aortic root and also provide antegrade flow to the carotid arteries and downstream arteries. Accordingly, ECMO reperfusion cannula 50 may be shortened compared with conventional ECMO cannulas, e.g., 5-15 cm, or preferably 8-10 cm.

As described above, when the patient is to be removed from ECMO, sheath 40 may be re-inserted over shaft 17 and advanced to collapse and retrieve expandable conduit 12. In this case, sheath 40 will first engage the plurality of angled legs that couple anchoring stent 21 of expandable conduit 12 to shaft 17, such that advancement of sheath 40 while retaining shaft 17 stationary will cause anchoring stent 21, and accordingly expandable conduit 12, to collapse inward and return to its reduced diameter, collapsed insertion state within sheath 40. As sheath 40 is further advanced distally over expandable conduit 12, sheath 40 will engage with and cause connection structure 19 to collapse inward and return to its collapsed insertion state, such that expandable conduit 12 is disposed within sheath 40. Extension cannula 10 and sheath 40 may then be removed through the hemostatic valve within second branch inlet 26.

Figure 2D:
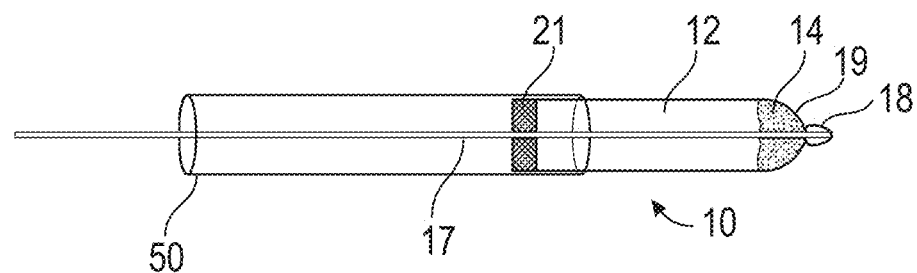
FIG. 2D is a schematic view illustrating use of the extension cannula of FIGS. 1A and 1B in an ECMO system.

FIG. 2D illustrates extension cannula 10 coupled to conventional ECMO reperfusion cannula 50 without in-line connector 20. As described above, in-line connector 20 is optional. Accordingly, the proximal end of conventional ECMO reperfusion cannula 50 may be coupled directly to the ECMO circuit.

Figure 3:
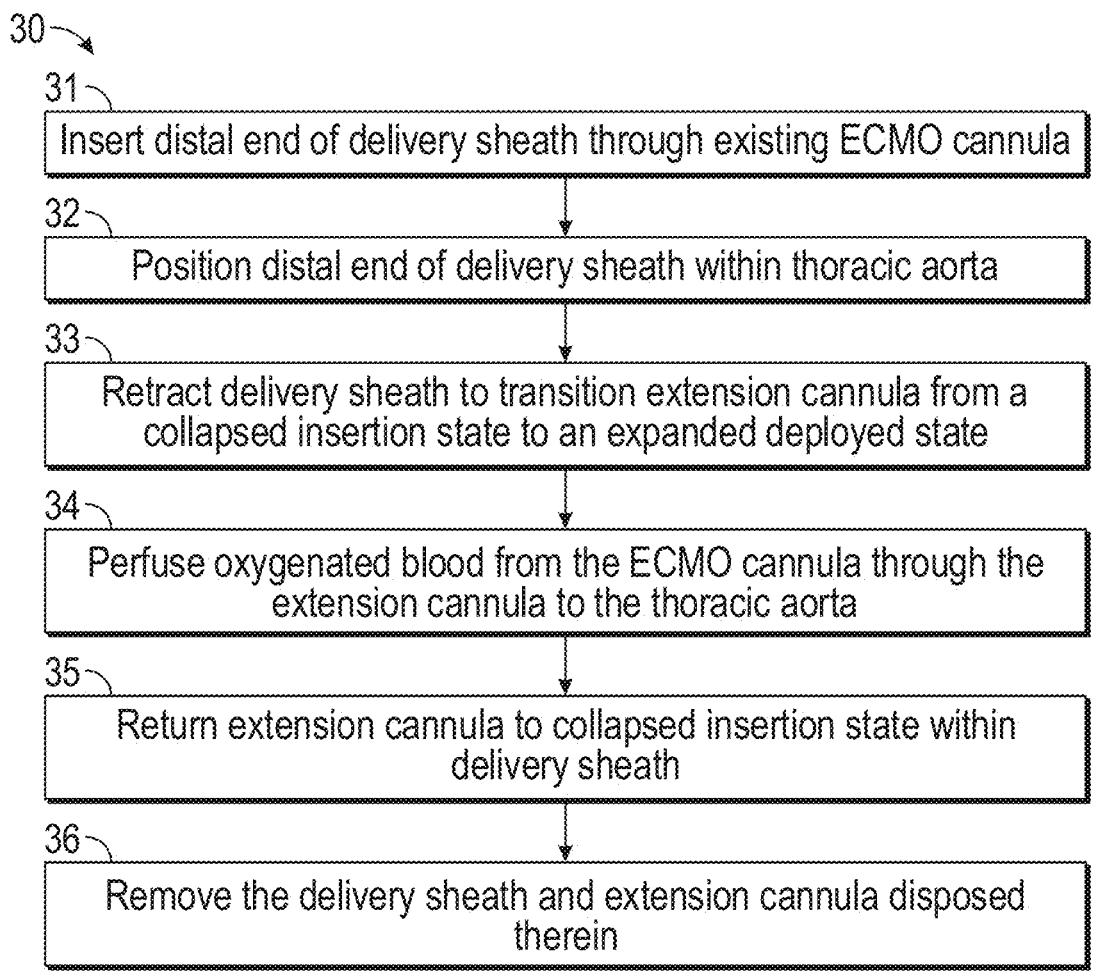
FIG. 3 is a flow chart of exemplary steps for improving perfusion during ECMO in accordance with the principles of the present invention.

Referring now to FIG. 3, a flow chart of exemplary steps for improving perfusion during ECMO in accordance with the principles of the present invention is provided. Some of the steps of method 30 may be further elaborated by referring to FIGS. 4A and 4B. Initially, the distal region of extension cannula 10 may be delivered to the target location within the thoracic aorta in a collapsed insertion state within sheath 40. For example, conventional ECMO cannula 50 may be inserted through the patient's femoral artery FA. Preferably, conventional ECMO cannula 50 is not yet coupled to ECMO machine 51 at this stage. Next, guidewire 41 may be inserted through ECMO cannula 50 until the distal end of guidewire 41 is advanced to the desired location within the patient's vasculature, e.g., within the thoracic aorta TA such as within the ascending aorta or in the vicinity of the aortic arch. At step 31, the distal end of sheath 40, having expandable conduit 12 disposed therein in a collapsed insertion state, is advanced through ECMO cannula 50, e.g., over guidewire 41, via the lumen of hypotube 17. The distal end of sheath 40 may then be advanced until it is positioned at the desired central location within the patient's vasculature at step 32. Guidewire 41 may then be removed through the proximal end of hypotube 17.

Figure 4A:
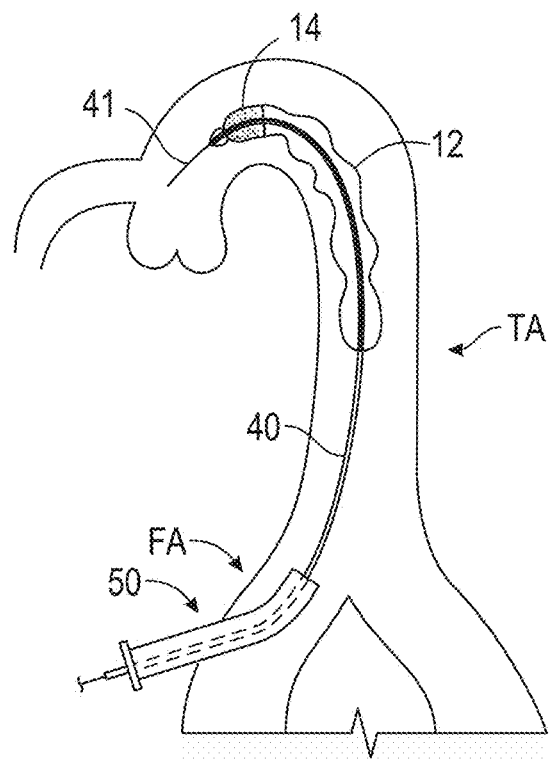
FIGS. 4A and 4B illustrate exemplary steps for improving perfusion during ECMO using the extension cannula of FIGS. 1A and 1B.

At step 33, sheath 40 is retracted relative to expandable conduit 12 slidably disposed within the lumen of sheath 40, while expandable conduit 12 remains stationary, causing connection structure 19, and accordingly at least a portion of expandable conduit 12, to transition from the collapsed insertion state to an expanded deployed state upon exposure from sheath 40, as shown in FIG. 4A. FIG. 4A illustrates expandable conduit 12 in a semi-expanded state within the patient's vasculature. Sheath 40 is further retracted relative to expandable conduit 12, causing anchoring stent 21 to transition from the collapsed insertion state to an expanded deployed state upon exposure from sheath 40 within ECMO cannula 50, thereby anchoring expandable conduit 12 to ECMO cannula 50. The proximal end of ECMO cannula 50 may then be coupled to ECMO machine 51, e.g., via tubing.

Figure 4B:
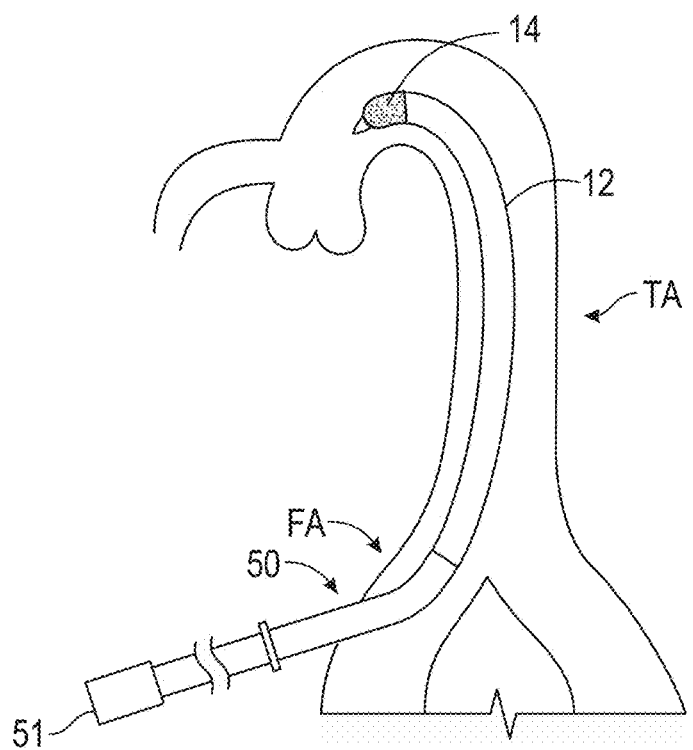

FIG. 4B illustrates expandable conduit 12 fully expanded within the patient's vasculature, e.g., when expandable conduit 12 is fully exposed from sheath 40 and blood flows from ECMO machine 51 through ECMO cannula 50 and into the lumen of expandable conduit 12. As described above, when expandable conduit 12 is fully deployed within the patient's vasculature, at step 34, oxygenated blood may be perfused from ECMO cannula 50 to the central location within the patient's vasculature, e.g., within the ascending aorta or in the vicinity of the aortic arch, via pores 14 at the distal region of expandable conduit 12. When the ECMO therapy is complete, at step 35, expandable conduit 12 may be returned to the collapsed insertion state within the lumen of sheath 40 as described above, and at step 36, sheath 40 and expandable conduit 12 disposed therein may be removed from the patient.

Figure 5A:
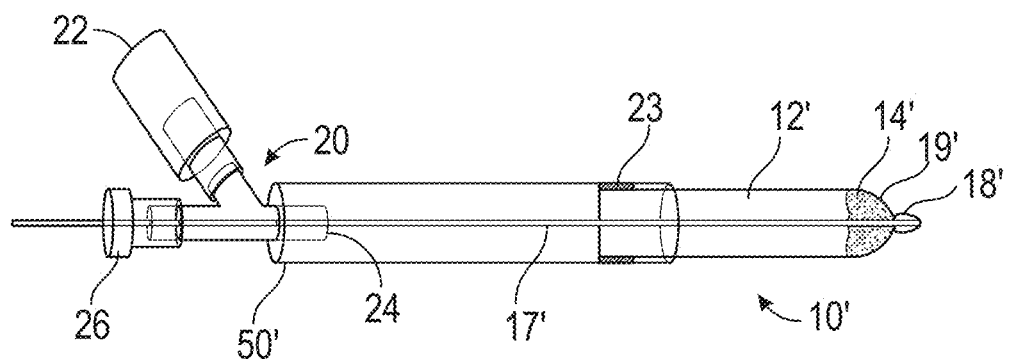
FIG. 5A is a schematic view illustrating use of an exemplary in-line connector with an alternative exemplary extension cannula in an ECMO system, constructed in accordance with the principles of the present invention, where a proximal end of the extension cannula is coupled to a conventional ECMO cannula.

Referring now to FIG. 5A, another alternative exemplary extension cannula is provided. Extension cannula 10' may be constructed similar to the extension cannula 10, except that the proximal end of expandable conduit 12' may be fixed to conventional ECMO reperfusion cannula 50' prior to insertion of extension cannula 10' into the patient. For example, as shown in FIG. 5A, the proximal end of expandable conduit 12' may be coupled to the inner surface of conventional ECMO reperfusion cannula 50' via coupling mechanism 23, e.g., an adhesive. Accordingly, extension cannula 10', conventional ECMO reperfusion cannula 50', and in-line connector 20, are advanced together into the patient, e.g., by guiding tip 18' of extension cannula 10' via hypotube 17', to position pores 14' of expandable conduit 12' in the vicinity of the aortic root, as described in further detail below.

Figure 5B:
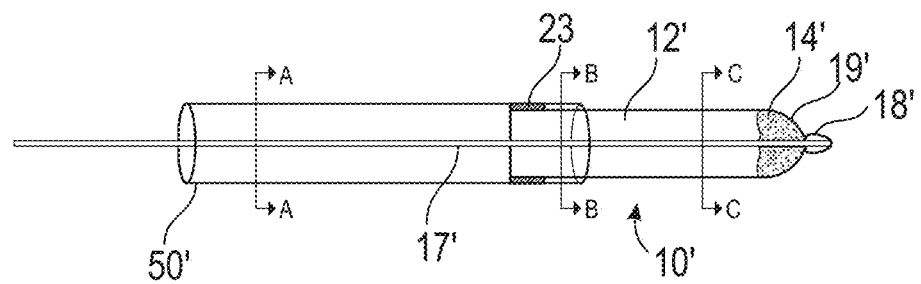
FIG. 5B is a schematic view illustrating use of the extension cannula of FIG. 5A in an ECMO system without an in-line connector.
Figure 6C:
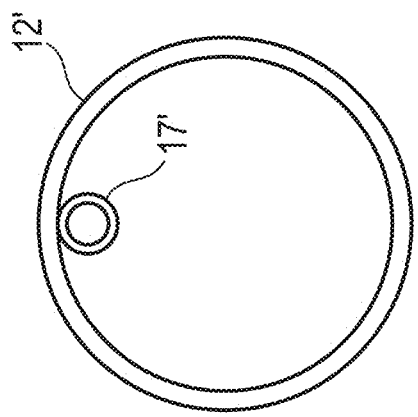
FIGS. 6A to 6C are cross-sectional views of the extension cannula of FIG. 5B.
Figure 6B:
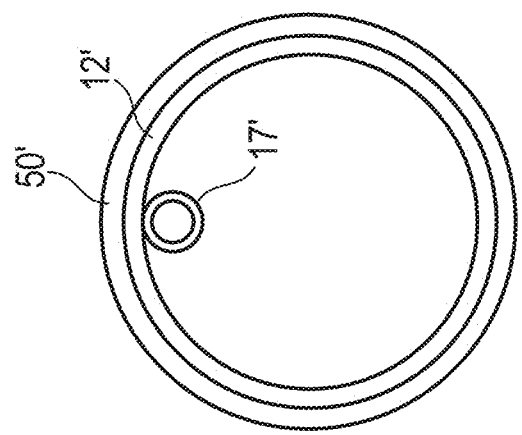
Figure 6A:
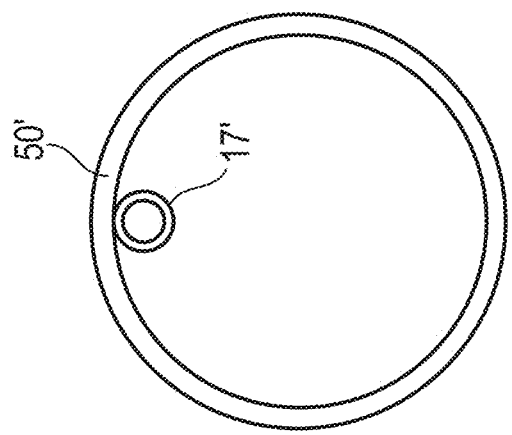

FIG. 5B illustrates extension cannula 10' coupled to conventional ECMO reperfusion cannula 50' without in-line connector 20. As described above, in-line connector 20 is optional. Accordingly, the proximal end of conventional ECMO reperfusion cannula 50' may be coupled directly to the ECMO circuit. As shown in FIGS. 6A to 6C, hypotube 17' may be positioned on a single side within the lumens of expandable conduit 12' and ECMO cannula 50'. Specifically, FIG. 6A illustrates a cross-sectional view of extension cannula 10' along line A-A of FIG. 5B, FIG. 6B illustrates a cross-sectional view of extension cannula 10' along line B-B of FIG. 5B, and FIG. 6C illustrates a cross-sectional view of extension cannula 10' along line C-C of FIG. 5B. As shown in FIG. 6A, hypotube 17' may be positioned against an inner wall of ECMO cannula 50' within the proximal region of ECMO cannula 50'. As shown in FIG. 6B, hypotube 17' may be positioned against an inner wall of expandable conduit 12' within the distal region of ECMO cannula 50', e.g., adjacent to where expandable conduit 12' is coupled to ECMO cannula 50' via coupling mechanism 81. As shown in FIG. 6C, hypotube 17' may be positioned against an inner wall of expandable conduit 12' throughout the length of expandable conduit 12'. Accordingly, hypotube 17' may extend from tip 18', and along an inner surface of hypotube 17' toward ECMO cannula 50'.

Figure 5C:
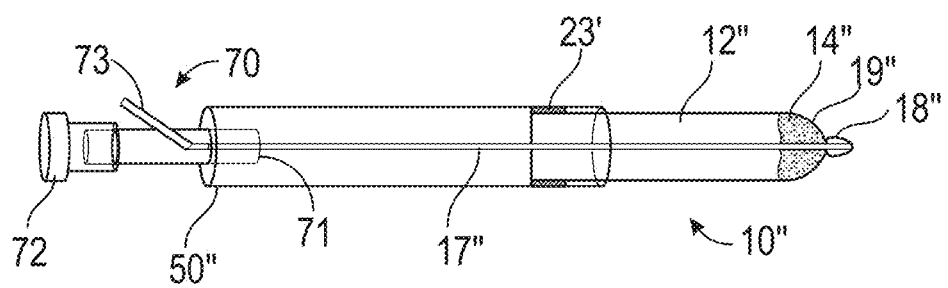
FIG. 5C is a schematic view illustrating use of an exemplary connector having a side arm with the extension cannula of FIG. 5A in an ECMO system.

Referring now to FIG. 5C, another exemplary connector for use with the extension cannulas described herein is provided. Connector 70 may have inlet 72 configured to be coupled to an outlet of a conventional ECMO machine for receiving oxygenated blood from an ECMO circuit, sidearm 73 extending at an angle from a side of connector 70, and outlet 71 configured to be coupled to a conventional ECMO cannula. Inlet 72 is in fluid communication with outlet 71, and may include an optional hemostatic valve. The fluid pathway extending between inlet 72 and outlet 71 thus permits oxygenated blood received from an ECMO circuit to flow to through the conventional ECMO cannula and expandable conduit 12". As shown in FIG. 5C, inlet 72 may be co-linear with outlet 71. Moreover, sidearm 73 is in fluid communication with the lumen of hypotube 17'", and also may have an optional hemostatic valve welded therein. Accordingly, sidearm 73 may have a lumen sized and shaped to receive a guidewire therethrough. In addition, sidearm 73 and hypotube 17'" may be sized and shaped to receive a stylet therein, the stylet configured to be inserted through sidearm 73 and hypotube 17'" to preserve the lumen of sidearm 73 and hypotube 17'" during operation and prevent clotting therein. Additionally, upon removal of the stylet, the guidewire may be reinserted through sidearm 73 and hypotube 17'" for removal of extension cannula 10".

Figure 7:
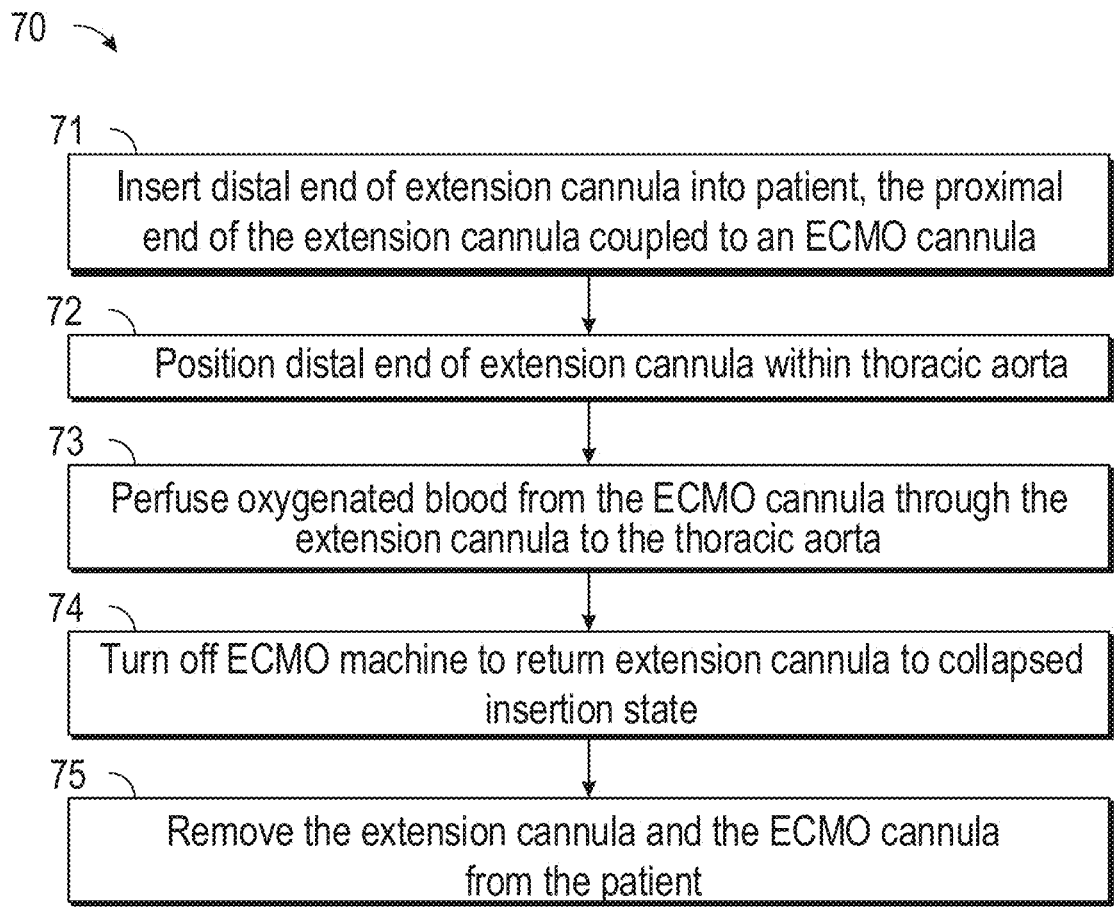
FIG. 7 is a flow chart of exemplary steps for improving perfusion during ECMO using the extension cannula of FIGS. 5A to 5C in accordance with the principles of the present invention.

Referring now to FIG. 7, a flow chart of exemplary steps for improving perfusion during ECMO using any one of the extension cannulas of FIGS. 5A to 5C is provided. Some of the steps of method 70 may be further elaborated by referring to FIGS. 8A and 8B, as well as FIGS. 9A to 9B, as described in further detail below. As described above, expandable conduit 12' is coupled to ECMO cannula 50' prior to insertion of extension cannula 10' and ECMO cannula 50' into the patient. Accordingly, referring to the extension cannula of FIG. 5B, hypotube 17' may extend from tip 18' proximally through the lumen of expandable conduit 12', and the lumen of ECMO cannula 50. Moreover, ECMO cannula 50' may be directly coupled to ECMO machine 51. Initially, guidewire 41 may be advanced through an incision in the patient's femoral artery FA until the distal end of guidewire 41 is advanced to the desired location within the patient's vasculature, e.g., within the thoracic aorta TA such as within the ascending aorta or in the vicinity of the aortic arch.

Figure 8A:
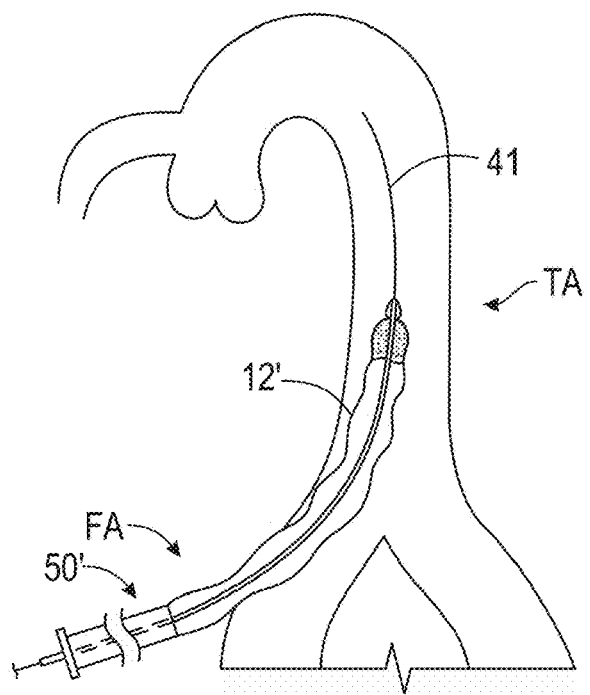
FIGS. 8A and 8B illustrate exemplary steps for improving perfusion during ECMO using the extension cannula of FIG. 5B.
Figure 8B:
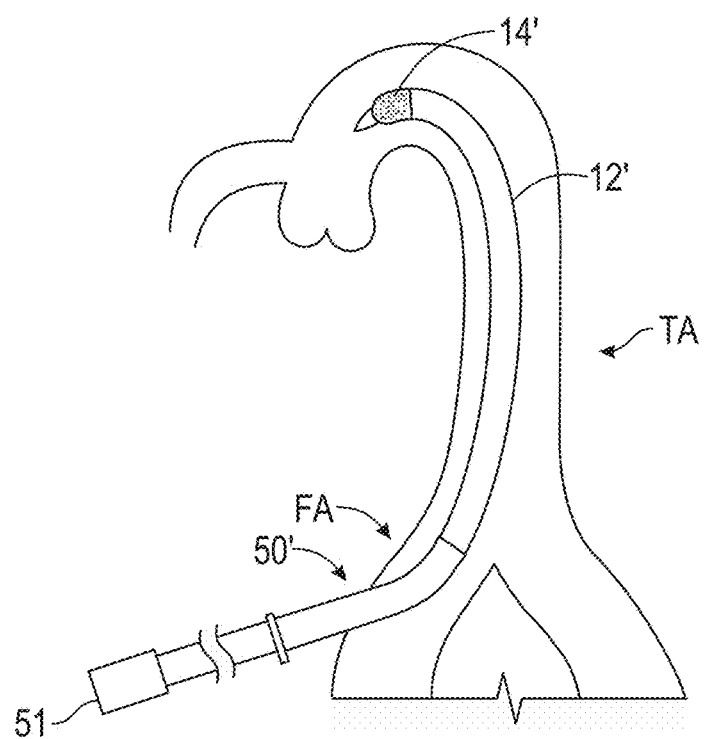

At step 71 the distal end of extension cannula 10', e.g., tip 18' of expandable conduit 12', is advanced over guidewire 41 via the lumen of hypotube 17', together with ECMO cannula 50', as shown in FIG. 8A. Extension cannula 10' and ECMO cannula 50 are advanced until expandable conduit 12' is positioned at the desired central location within the patient's vasculature at step 72, and ECMO cannula 50' is positioned within the patient's femoral artery FA, as shown in FIG. 8B. Guidewire 41 may then be removed through the proximal end of ECMO cannula 50', and the proximal end of ECMO cannula 50' may then be coupled to ECMO machine 51.

At step 73, oxygenated blood may be perfused from ECMO machine 51 through the lumen of expandable conduit 12' via ECMO cannula 50', thereby causing expandable conduit 12' to fully expanded within the patient's vasculature as shown in FIG. 8B, to the central location within the patient's vasculature, e.g., within the ascending aorta or in the vicinity of the aortic arch, via pores 14' at the distal region of expandable conduit 12'. As will be understood by a person of ordinary skill in the art, pores 14' of expandable conduit 12' may be positioned within the descending aorta, e.g., the portion of the descending aorta approaching the level of the diaphragm from beneath the thoracic cavity or the portion of the descending aorta above the diaphragm. When the ECMO therapy is complete, at step 74, the ECMO machine may be turned off, such that blood no longer flows through expandable conduit 12', thereby causing expandable conduit 12' to return to a semi-collapsed state, and at step 75, extension cannula 10' and ECMO cannula 50' may be removed from the patient.

Figure 9A:
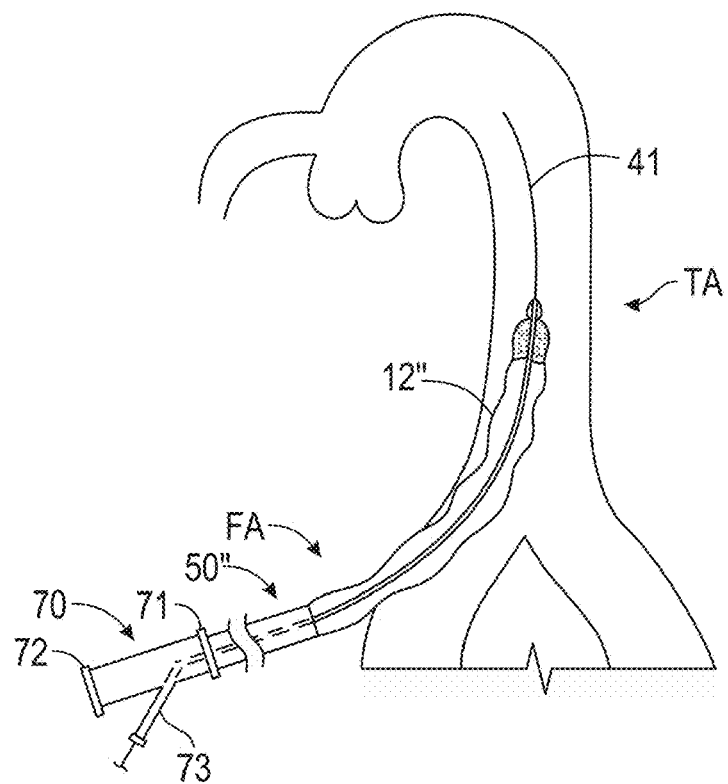
FIGS. 9A and 9B illustrate exemplary steps for improving perfusion during ECMO using the extension cannula of FIG. 5C.
Figure 9B:
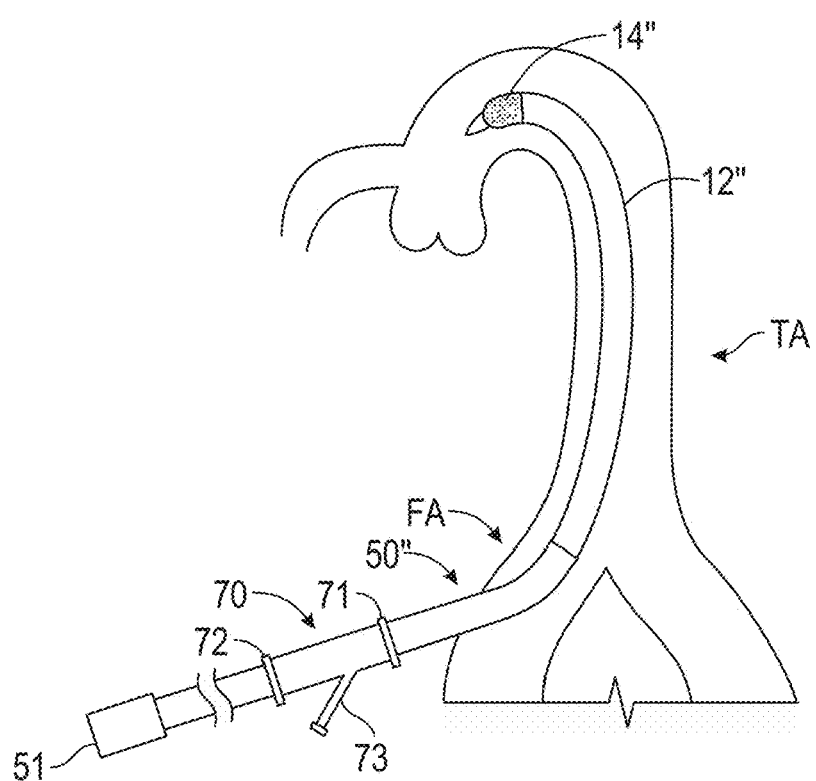

Referring now to FIGS. 9A and 9B, exemplary steps for improving perfusion during ECMO using the extension cannula of FIG. 5C is provided. Specifically, method steps 71-75 of FIG. 7 described above may be used to deliver extension cannula 10" having connector 70 coupled thereto for improving perfusion during ECMO. For example, at step 71 the distal end of extension cannula 10", e.g., tip 18" of expandable conduit 12", is advanced over guidewire 41 via the lumen of hypotube 17", together with ECMO cannula 50" and connector 70, as shown in FIG. 9A. Extension cannula 10" and ECMO cannula 50" are advanced until expandable conduit 12" is positioned at the desired central location within the patient's vasculature at step 72, and ECMO cannula 50" is positioned within the patient's femoral artery FA, such that guidewire 41 extends out of sidearm 73. Guidewire 41 may then be removed through sidearm 73. A stylet may then be inserted through sidearm 73 and hypotube 17", e.g., until the end of the stylet is adjacent to tip 18" of extension cannula 10", to thereby prevent blood from entering hypotube 17" and clotting therein during operation. Alternatively, an end cap may be coupled to sidearm 73. Inlet 72 of connector 70 may then be coupled to ECMO machine 51, as shown in FIG. 9B.

As described above, at step 73, oxygenated blood may be perfused from ECMO machine 51 through the lumen of expandable conduit 12" via connector 70 and ECMO cannula 50", thereby causing expandable conduit 12" to fully expanded within the patient's vasculature as shown in FIG. 9B, to the central location within the patient's vasculature, e.g., within the ascending aorta or in the vicinity of the aortic arch, via pores 14" at the distal region of expandable conduit 12". When the ECMO therapy is complete, at step 74, the ECMO machine may be turned off, such that blood no longer flows through expandable conduit 12", thereby causing expandable conduit 12" to return to a semi-collapsed state. The stylet may then be removed from sidearm 73 and hypotube 17", guidewire 41 may be reinserted through sidearm 73 and hypotube 17". At step 75, extension cannula 10" and ECMO cannula 50" may be removed from the patient, e.g., over guidewire 41. Existing long venous cannulas do not have a proximal side-connecting Luer lock, and thus, if such long venous cannulas were to be used in the arterial position, it would not provide antegrade perfusion of the leg. In contrast, existing arterial cannulas may include a proximal side-connecting Luer lock; however, such arterial cannulas are shorter than the existing long venous cannulas. Accordingly, the custom built extension cannulas described herein provide a proximal side connecting Luer lock on a long arterial cannula.

Figure 10:
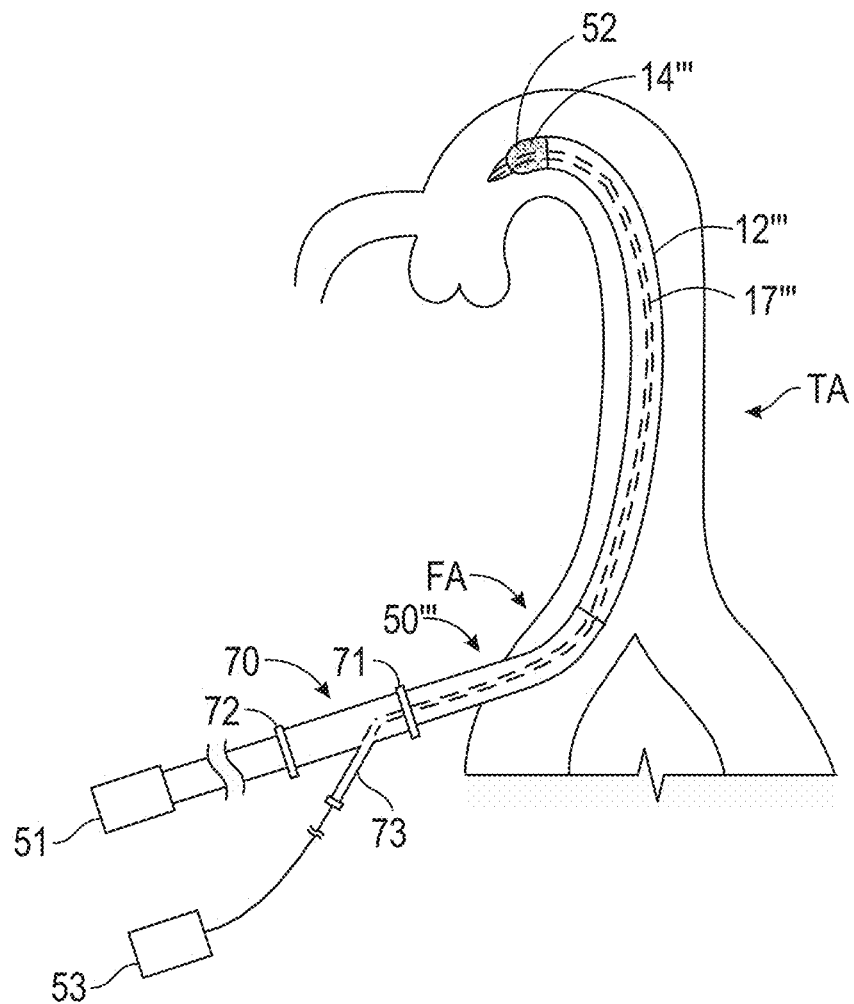
FIG. 10 illustrates an alternative exemplary extension cannula in an ECMO system having one or more sensors, constructed in accordance with the principles of the present invention, where a proximal end of the extension cannula is coupled to a conventional ECMO cannula.

Referring now to FIG. 10, another alternative exemplary extension cannula is provided. Extension cannula 10''' may be constructed similar to the extension cannula 10, 10' except that extension cannula 10''' may include one or more sensors 52 disposed on the distal region of expandable conduit 12''' for measuring one or more physiological parameters within the patient's vasculature. For example, sensors 52 may be a pressure sensor, flow sensor, and/or an oxygen saturation sensor. Accordingly, in addition to a guidewire/stylet lumen, hypotube 17''' may have another separate lumen extending therethrough, sized and shaped to receive electrical wires for coupling sensors 52 to console 53, e.g., via sidearm 73, for providing pressure and/or oxygen saturation readouts.

Figure 11A:
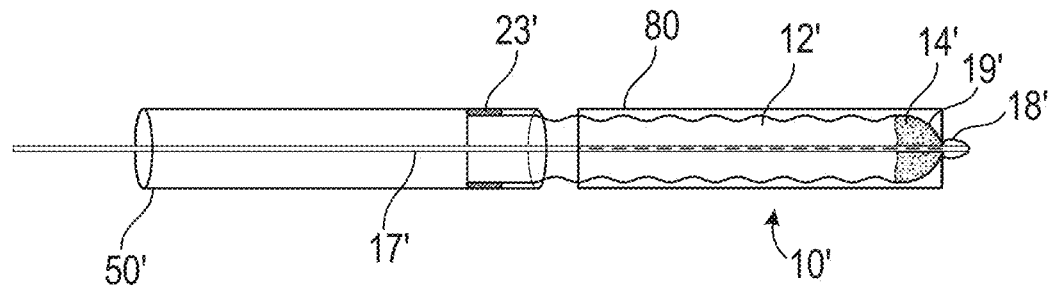
FIGS. 11A and 11B are schematic views illustrating the extension cannula of FIG. 5B with a peel away introducer constructed in accordance with the principles of the present invention.
Figure 11B:
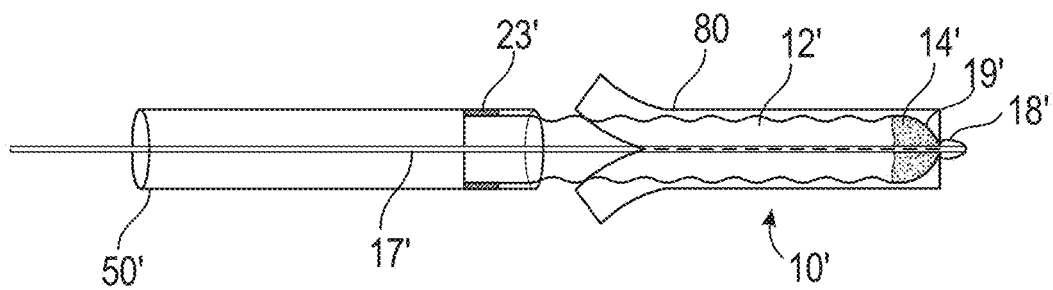

Referring now to FIGS. 11A and 11B, a delivery system for delivering extension cannula 10' is provided. As shown in FIGS. 11A and 11B, at least a portion of expandable conduit 12' may be disposed within peel-away introducer 80. For example, introducer 80 may extend from tip 18' of expandable conduit 12' proximally toward the proximal region of expandable conduit 12'. Preferably, introducer 80 extends along only a portion of expandable conduit 12'. Alternatively, introducer 80 may extend along the entire length of expandable conduit 12'. Introducer 80 preferably has a diameter that is equal to or slightly less than the diameter of ECMO cannula 50', such that when introducer 80 is inserted through the patient's skin and into the artery, the arterial puncture is not larger than EMCO cannula 50' and insertion of ECMO cannula 50' into the arteriotomy after the peel-away introducer has been removed will be hemostatic without bleeding. Introducer 80 may be retracted proximally relative to expandable conduit 12' and peeled away from its proximal end as shown in FIG. 11B, external to the patient.

Figure 11C:
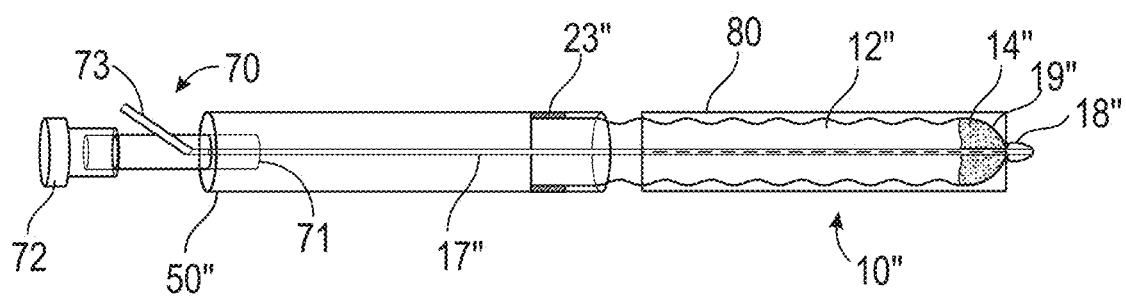
FIG. 11C is a schematic view illustrating the extension cannula of FIG. 5C with a peel away introducer constructed in accordance with the principles of the present invention.

As shown in FIG. 11C, peel-away introducer 80 also may be used to facilitate delivery of extension cannula 10" through the patient's skin and into the artery. For example, as shown in FIG. 11C, introducer 80 may extend from tip 18" of expandable conduit 12" proximally toward the proximal region of expandable conduit 12". Preferably, introducer 80 extends along only a portion of expandable conduit 12". Alternatively, introducer 80 may extend along the entire length of expandable conduit 12". As will be understood by a person having ordinary skill in the art, peel-away introducer may be used to facilitate delivery of the other extension cannulas described herein where the expandable conduit is prefixed to the ECMO cannula. For example, introducer 80 may be used to deliver the extension cannulas described herein that are coupled to in-line connector 20.

Referring now to FIG. 12, a flow chart of exemplary steps for improving perfusion during ECMO using the delivery system of any one of FIGS. 11A to 11C is provided. Some of the steps of method 120 may be further elaborated by referring to FIGS. 13A to 13D, as described in further detail below. As described above, at least a portion of expandable conduit 12' is disposed within peel-away introducer 80, such that introducer 80 extends from tip 18' proximally towards the proximal region of expandable conduit 12'. Initially, guidewire 41 may be advanced through an incision in the patient's femoral artery FA until the distal end of guidewire 41 is advanced to the desired location within the patient's vasculature, e.g., within the thoracic aorta TA such as within the ascending aorta or in the vicinity of the aortic arch.

Figure 13A:
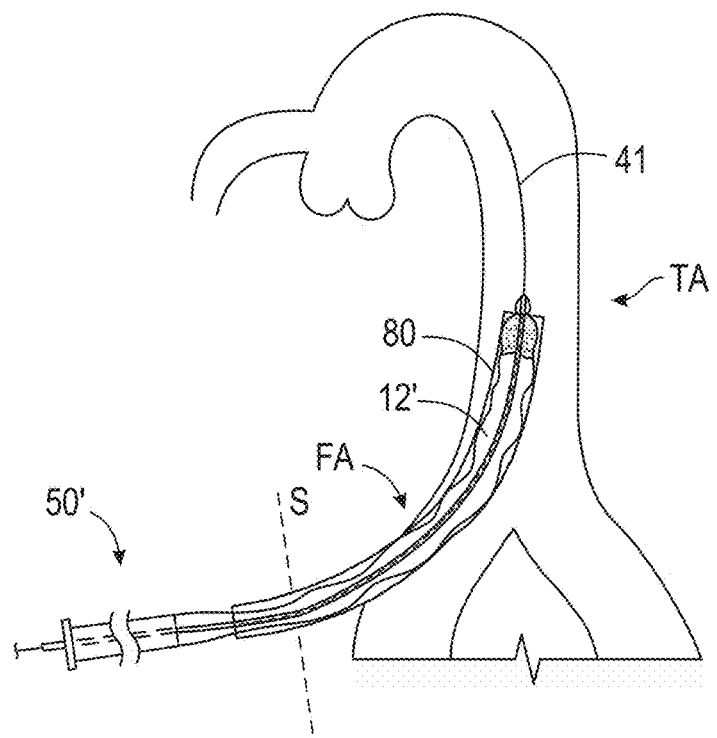
FIGS. 13A to 13D illustrate exemplary steps for improving perfusion during ECMO using the extension cannula of FIG. 5B.

At step 121 the distal end of extension cannula 10', e.g., tip 18' of expandable conduit 12', disposed within introducer 80, is advanced over guidewire 41 via the lumen of hypotube 17', together with ECMO cannula 50', as shown in FIG. 13A. At step 122, extension cannula 10', introducer 80, and ECMO cannula 50' are advanced until introducer 80 is positioned through the patient's skin S and through femoral artery FA, such that the distal end of expandable conduit 12' is disposed within the artery. The proximal end of introducer 80 will remain external to the patient. As described above, introducer 80 may be disposed over only a portion of expandable conduit 12', and thus, when introducer 80 is inserted through the patient's vasculature as far as it can be while its proximal end remains external to the patient, the distal end of expandable conduit 12' may not yet be disposed within the desired location within the patient's vasculature, e.g., within the vicinity of the aortic arch.

Figure 13B:
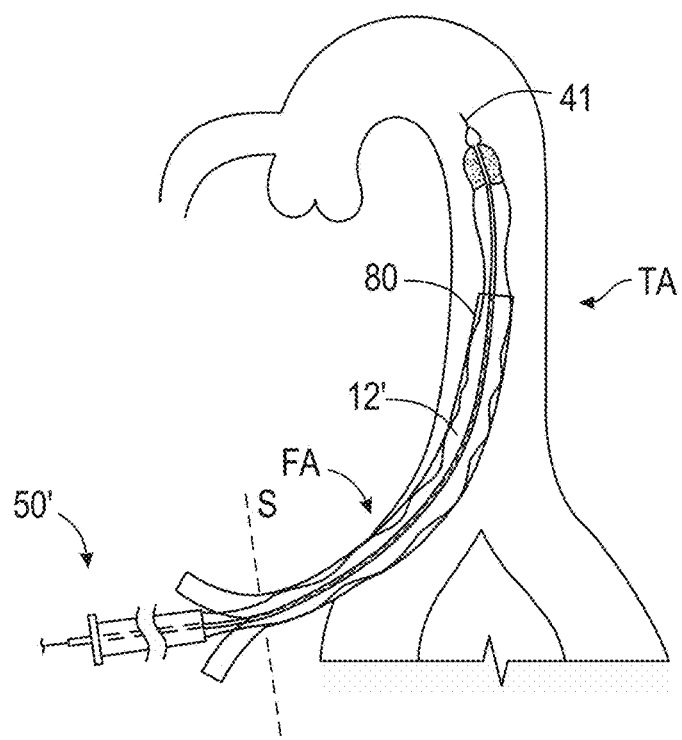
Figure 13C:
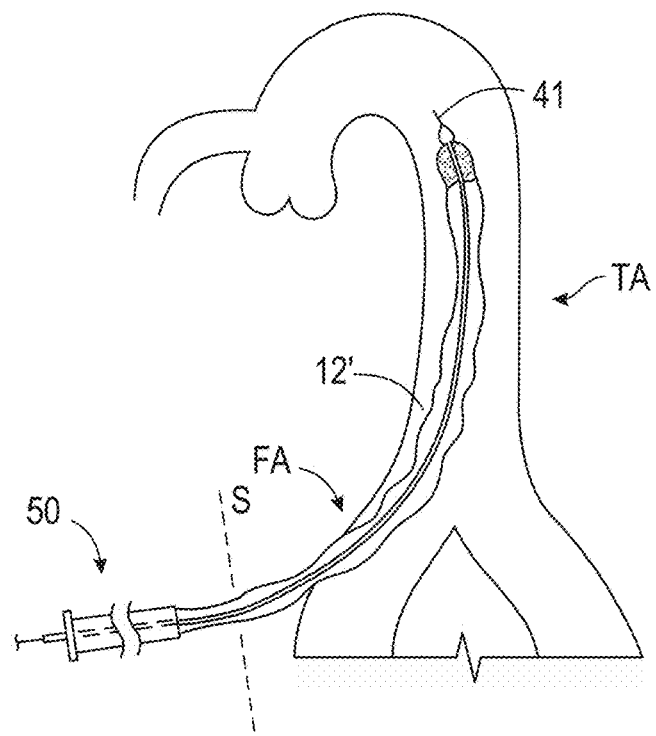
Figure 13D:
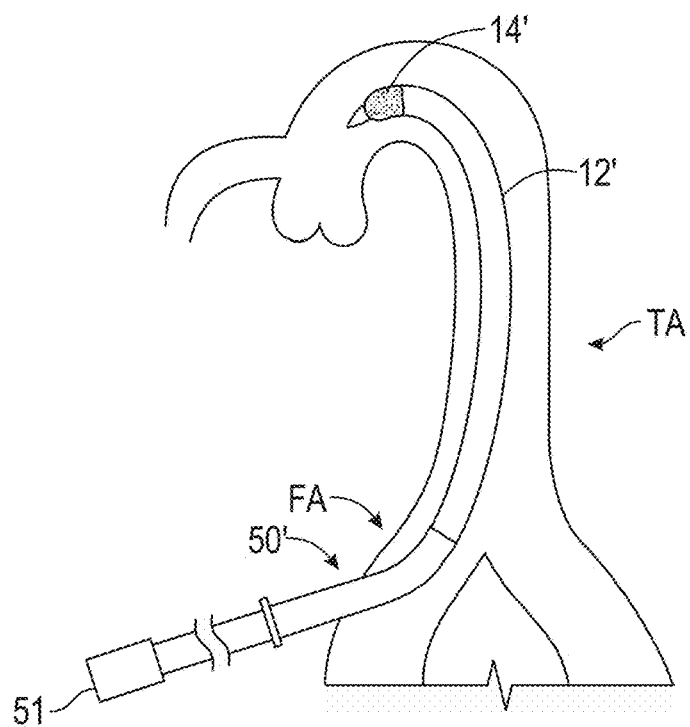

At step 123, introducer 80 may be retracted proximally relative to expandable conduit 12', while expandable conduit 12' remains stationary within the patient's vasculature. As introducer 80 is retracted, it may simultaneously be peeled away from expandable conduit 12' along its proximal end, as shown in FIG. 13B, until introducer 80 is completely removed from expandable conduit 12', as shown in FIG. 13C. Once introducer 80 is completely removed from expandable conduit 12', at step 124, the extension cannula may be further inserted into the patient until the distal end of expandable conduit 12' is positioned at the desired central location within the patient's vasculature, and ECMO cannula 50' is positioned within the patient's femoral artery FA, as shown in FIG. 13D. Guidewire 41 may then be removed through the proximal end of ECMO cannula 50', and the proximal end of ECMO cannula 50' may then be coupled to ECMO machine 51.

At step 125, oxygenated blood may be perfused from ECMO machine 51 through the lumen of expandable conduit 12' via ECMO cannula 50', thereby causing expandable conduit 12' to fully expanded within the patient's vasculature as shown in FIG. 13D, to the central location within the patient's vasculature, e.g., within the ascending aorta or in the vicinity of the aortic arch, via pores 14' at the distal region of expandable conduit 12'. As will be understood by a person of ordinary skill in the art, pores 14' of expandable conduit 12' may be positioned within the descending aorta, e.g., the portion of the descending aorta approaching the level of the diaphragm from beneath the thoracic cavity or the portion of the descending aorta above the diaphragm. When the ECMO therapy is complete, at step 126, the ECMO machine may be turned off, such that blood no longer flows through expandable conduit 12', thereby causing expandable conduit 12' to return to a semi-collapsed state, and at step 127, extension cannula 10' and ECMO cannula 50' may be removed from the patient.

As described above, in some embodiments, introducer 80 may extend along the entire length of expandable conduit 12'. Accordingly, when introducer 80 is inserted through the patient's vasculature as far as it can be while its proximal end remains external to the patient, the distal end of expandable conduit 12' may be disposed within the desired location within the patient's vasculature, e.g., within the vicinity of the aortic arch, such that upon removal of introducer 80 from expandable conduit 12', the extension cannula only needs to be further inserted into the patient until ECMO cannula 50' is positioned within the patient's femoral artery FA.

Figure 14A:
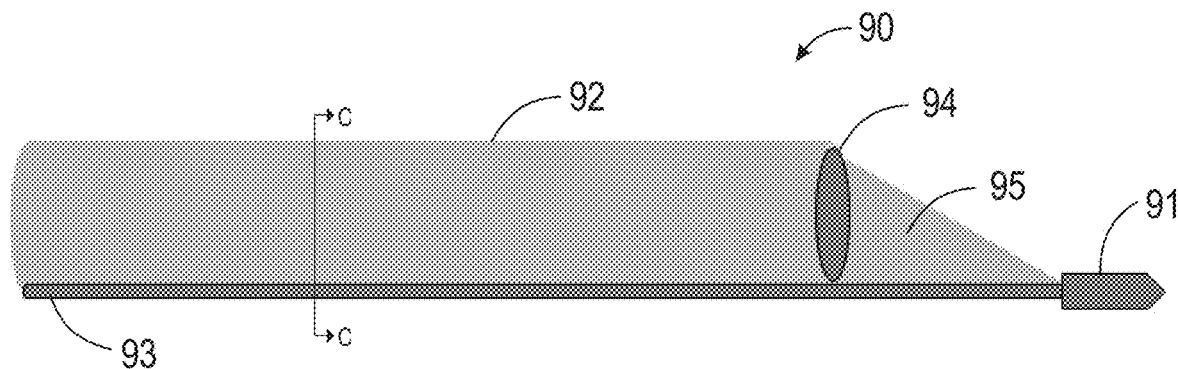
FIGS. 14A and 14B illustrate alternative extension cannulas having an external hypotube constructed in accordance with the principles of the present invention.

Referring now to FIG. 14A, an additional alternative extension cannula is provided. As shown in FIG. 14A, extension cannula 90 may include expandable conduit 92 and elongated shaft 93, e.g., a hypotube, extending from tip 91 at the distal end of extension cannula 90 towards the proximal end of extension cannula 90. Hypotube 93 is formed of a material, e.g., stainless steel rod, having sufficient rigidity to permit extension cannula 90 to be advanced through a conventional ECMO reperfusion cannula so that the distal region of expandable conduit 92 may be disposed with its outlet extending beyond a patient's renal arteries, and preferably extending in a patient's ascending aorta or in the vicinity of the aortic arch. For example, hypotube 93 may have a lumen sized and shaped to receive a guidewire therethrough, such that extension cannula 90 may be advanced through the conventional ECMO reperfusion cannula to the target location over a guidewire via the lumen of hypotube 93. As shown in FIG. 14C, which is a cross-sectional view of extension cannula 90 along line C-C of FIG. 14A, hypotube 93 may be positioned on a single, lateral side of expandable conduit 92. For example, as shown in FIG. 14C, hypotube 93 may be positioned along an inner wall of expandable conduit 92. Accordingly, hypotube 93 may extend from tip 91, and along an inner surface of expandable conduit 92 toward the ECMO cannula. Moreover, hypotube 93 further may extend along an inner surface of the ECMO cannula. Accordingly, hypotube 93 is not in the blood flow path through the lumen of expandable conduit 12. In some embodiments, instead of extending from tip 91 along an inner surface of expandable conduit 12, hypotube 93 may extend from tip 91 along an outer surface of expandable conduit 12, and accordingly, along an outer surface of the ECMO cannula, or alternatively, hypotube 93 may be embedded within the biocompatible material forming expandable conduit 12, e.g., the membrane of expandable conduit 12, such that hypotube 93 extends from tip 91 and through the membrane of expandable conduit 12 towards the ECMO cannula.

Referring again to FIG. 14A, the distal end of hypotube 93 may include atraumatic tip 91, which may be coupled to the distal region of expandable conduit 92. In addition, as shown in FIG. 14A, extension cannula 90 further may include circumferential support 94 positioned at the distal region of expandable conduit 92 to facilitate expansion of expandable conduit 92 within the patient's vasculature. Support 94 may be self-expandable between a collapsed delivery state and an expanded deployed state, e.g., upon exposure from the delivery sheath. As shown in FIG. 14A, support 94 may have a circumferential profile in the expanded deployed state. Support 94 may be embedded within the biocompatible material forming expanding conduit 92. Additionally or alternatively, support 94 may be coupled to the inner surface of expandable conduit 92 or to the outer surface of expandable conduit 92, or both. Moreover, in some embodiments, support 94 may also be coupled to hypotube 93. In one embodiment, support 94 is not self-expandable, such that support 94 transitions from the collapsed delivery state to the expanded deployed state when blood flows through the lumen of expandable conduit 94, thereby causing expandable conduit 92 to fill with blood. In some embodiments, extension cannula 90 may not include support 94.

Expandable conduit 92 is made of a soft flexible material, such as polyethylene, polyurethane, or nylon, and may include a plurality of pores 95 at its distal region that permit blood to perfuse through the material as the flow is directed through the lumen of expandable conduit 92. Pores 95 may be sized and shaped such that, as blood flows from the ECMO machine and through the conventional ECMO reperfusion cannula and the lumen of expandable conduit 92, the blood flow exits expandable conduit 92 via pores 95, while causing expandable conduit 92 to fill with blood and transition from a collapsed delivery state to the expanded deployed state. In some embodiments, the biocompatible polymer coating may include additional pores proximal to pores 95 that permit blood to perfuse laterally through the material, thereby reducing jetting from pores 95. Moreover, expandable conduit 92 has a length sufficient to extend from the outlet of the conventional ECMO reperfusion cannula to a position above the patient's renal arteries, and more preferably, into the thoracic aorta, e.g., 15-120 cm, or preferably 20-80 cm or 30-50 cm. Notably, the lightweight sock-like structure provides advantages including, for example, ease of deployment through tortuous or diseased aortas, as well as no impingement on the spinal cord as most patients are lying flat such that use of a rigid cannula may impinge on the spinal cord.

Figure 14B:
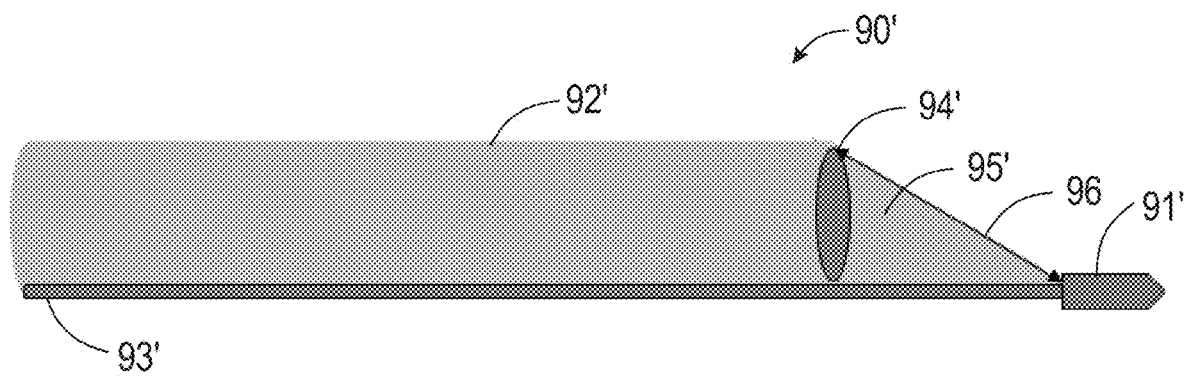
Figure 14C:
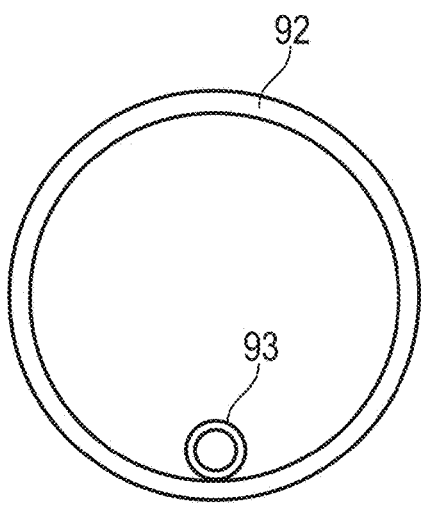
FIG. 14C is a cross-sectional view of the extension cannula of FIG. 14A.

Referring now to FIG. 14B, an additional alternative extension cannula is provided. Extension cannula 90' may be constructed similar to extension cannula 90, except that extension cannula 90' further may include connection structure 96, e.g., one or more umbrella-like struts, extending between tip 91' and support 94' to thereby provide reinforcement support at the distal region of extension cannula 90'. Connection structure 96 may be self-expandable between a collapsed delivery state and an expanded deployed state, e.g., upon exposure from the delivery sheath. As shown in FIG. 14B, connection structure 96 may have a linear shape in the expanded deployed state. Connection structure 96 may be embedded within the biocompatible material forming expanding conduit 92. Additionally or alternatively, connection structure 96 may be coupled to the inner surface of expandable conduit 92 or to the outer surface of expandable conduit 92, or both. In one embodiment, connection structure 96 is not self-expandable, such that connection structure 96 transitions from the collapsed delivery state to the expanded deployed state when blood flows through the lumen of expandable conduit 92, thereby causing expandable conduit 92 to fill with blood.

Figure 15A:
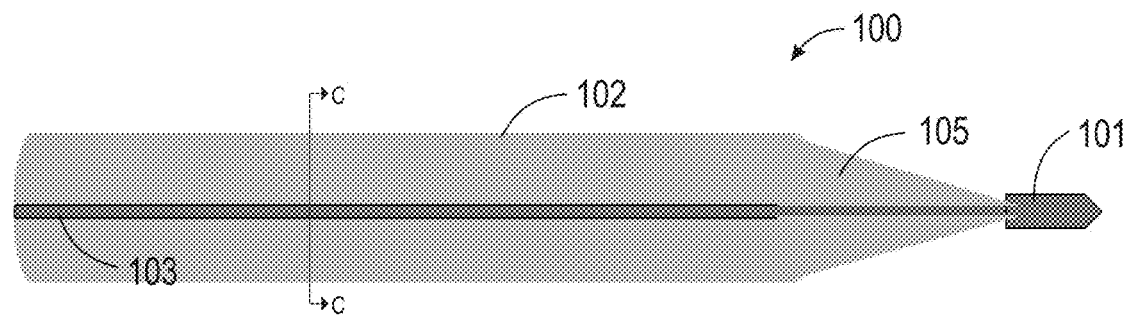
FIGS. 15A and 15B illustrate alternative extension cannulas having a central hypotube constructed in accordance with the principles of the present invention.

Referring now to FIG. 15A, an additional alternative extension cannula is provided. As shown in FIG. 15A, extension cannula 100 may include expandable conduit 102 and elongated shaft 103, e.g., a hypotube, extending from atraumatic tip 101 at the distal end of extension cannula 100 towards the proximal end of extension cannula 100. Hypotube 103 is formed of a material, e.g., stainless steel rod, having sufficient rigidity to permit extension cannula 100 to be advanced through a conventional ECMO reperfusion cannula so that the distal region of expandable conduit 102 may be disposed with its outlet extending beyond a patient's renal arteries, and preferably extending in a patient's ascending aorta or in the vicinity of the aortic arch. For example, hypotube 103 may have a lumen sized and shaped to receive a guidewire therethrough, such that extension cannula 100 may be advanced through the conventional ECMO reperfusion cannula to the target location over a guidewire via the lumen of hypotube 103. As shown in FIG. 15C, which is a cross-sectional view of extension cannula 100 along line C-C of FIG. 15A, hypotube 103 may be positioned at a central position within the lumen of expandable conduit 102. Specifically, as shown in FIG. 15A, hypotube 103 may extend along the longitudinal axis of extension cannula 100, while centered within the lumen of expandable conduit 102 to provide more stability in terms of cannula movement in the aorta. Accordingly, hypotube 103 may extend from tip 101, and through the lumen of expandable conduit 103 toward the ECMO cannula. Moreover, hypotube 103 further may extend through the lumen of the ECMO cannula. Hypotube 103 does not form part of the blood flow path through the lumen of expandable conduit 102.

Expandable conduit 102 is made of a soft flexible material, such as polyethylene, polyurethane, or nylon, and may include a plurality of pores 105 at its distal region that permit blood to perfuse through the material as the flow is directed through the lumen of expandable conduit 102. Pores 105 may be sized and shaped such that, as blood flows from the ECMO machine and through the conventional ECMO reperfusion cannula and the lumen of expandable conduit 102, the blood flow exits expandable conduit 102 via pores 105, while causing expandable conduit 102 to fill with blood and transition from a collapsed delivery state to the expanded deployed state. In some embodiments, the biocompatible polymer coating may include additional pores proximal to pores 105 that permit blood to perfuse laterally through the material, thereby reducing jetting from pores 105. Moreover, expandable conduit 102 has a length sufficient to extend from the outlet of the conventional ECMO reperfusion cannula to a position above the patient's renal arteries, and more preferably, into the thoracic aorta, e.g., 15-120 cm, or preferably 20-80 cm or 30-50 cm. Notably, the lightweight sock-like structure provides advantages including, for example, ease of deployment through tortuous or diseased aortas, as well as no impingement on the spinal cord as most patients are lying flat such that use of a rigid cannula may impinge on the spinal cord.

Figure 15B:
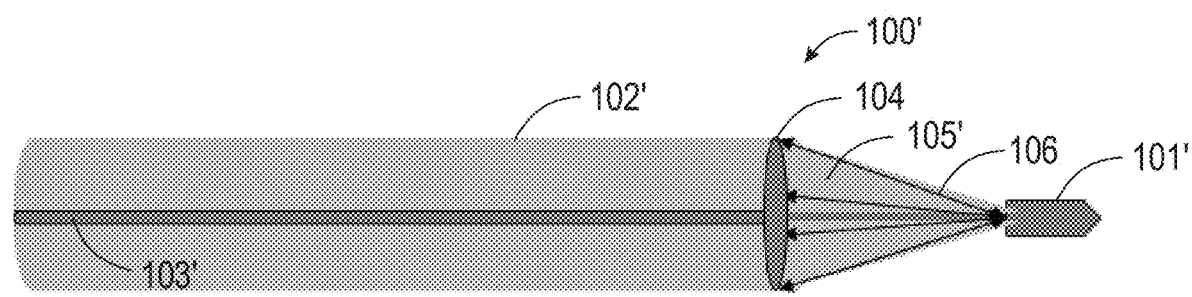
Figure 15C:
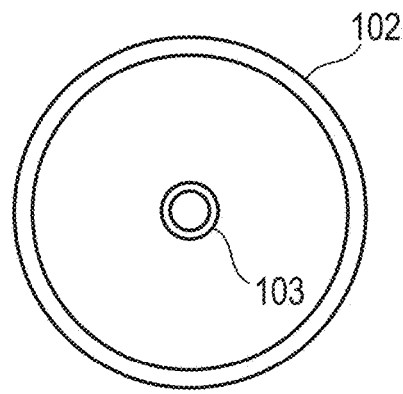
FIG. 15C is a cross-sectional view of the extension cannula of FIG. 15A.

Referring now to FIG. 15B, an additional alternative extension cannula is provided. Extension cannula 100' may be constructed similar to extension cannula 100, except that extension cannula 100' further may include circumferential support 104 and connection structure 105, e.g., one or more umbrella-like struts, extending between tip 101' and support 104 to thereby provide reinforcement support at the distal region of extension cannula 100'. As shown in FIG. 15B, support 104 may be positioned at the distal region of expandable conduit 102' to facilitate expansion of expandable conduit 102' within the patient's vasculature. Support 104 may be self-expandable between a collapsed delivery state and an expanded deployed state, e.g., upon exposure from the delivery sheath. As shown in FIG. 15B, support 104 may have a circumferential profile in the expanded deployed state. Support 104 may be embedded within the biocompatible material forming expanding conduit 102'. Additionally or alternatively, support 104 may be coupled to the inner surface of expandable conduit 102' or to the outer surface of expandable conduit 102', or both. In one embodiment, support 104 is not self-expandable, such that support 104 transitions from the collapsed delivery state to the expanded deployed state when blood flows through the lumen of expandable conduit 104, thereby causing expandable conduit 102' to fill with blood. In some embodiments, extension cannula 100 of FIG. 15A also may include a circumferential support.

Connection structure 105 may be self-expandable between a collapsed delivery state and an expanded deployed state, e.g., upon exposure from the delivery sheath. As shown in FIG. 15B, connection structure 105 may have a linear shape in the expanded deployed state. alternatively, connection structure 105 may have a curved shape in the expanded deployed state. Connection structure 105 may be embedded within the biocompatible material forming expanding conduit 102'. Additionally or alternatively, connection structure 105 may be coupled to the inner surface of expandable conduit 102' or to the outer surface of expandable conduit 102', or both. In one embodiment, connection structure 105 is not self-expandable, such that connection structure 105 transitions from the collapsed delivery state to the expanded deployed state when blood flows through the lumen of expandable conduit 102', thereby causing expandable conduit 102' to fill with blood.

Figure 16A:
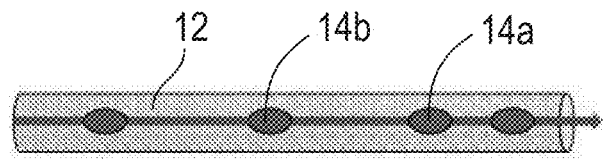
FIG. 16A to 16C illustrate various arrangements of the multiplicity of pores of the extension cannula in accordance with the principles of the present invention.
Figure 16B:
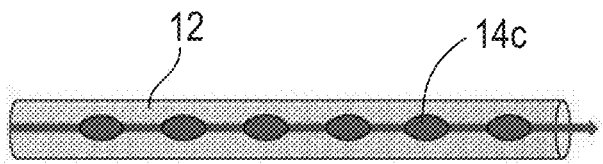
Figure 16C:
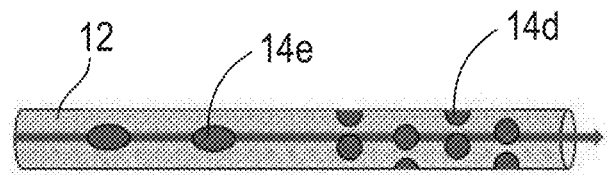

Referring now to FIGS. 16A to 16C, the extension cannulas described herein may include various arrangements and configurations of pores disposed on at least the distal region of the expandable conduit, e.g., expandable conduit 12, 12', 12'', 12''', 92, 92', 102, 102', the pores sized and shaped to permit blood flow therethrough to thereby avoid blood stasis or clotting along the length of the cannula and to more evenly distribute flow in the aorta, thereby also avoiding loading of the left ventricle. As shown in FIG. 16A, the plurality of pores may include first plurality of pores 14a and second plurality of pores 14b, which may have a longitudinally extending shape, e.g., oval shape. Moreover, pores 14a and pores 14b may be arranged laterally along the length of at least the distal region of the expandable conduit, such that pores 14b are proximal to pores 14a. In addition, pores 14a may be disposed spatially apart from each other along the expandable conduit by a distance that is less than the distance pores 14b are spatially disposed apart by along the expandable conduit.

As shown in FIG. 16B, the plurality of pores may include pores 14c, which may have a longitudinally extending shape, e.g., oval shape, and may be equally spatially disposed from each other along the length of at least the distal region of the expandable conduit.

As shown in FIG. 16C the plurality of pores may include first plurality of pores 14d and second plurality of pores 14e. Pores 14d may have a circular shape, and may be disposed circumferentially about at least the distal region of the expandable conduit. As shown in FIG. 16C, plurality of pores 14d may include multiple rows of circumferentially disposed pores. Although FIG. 16C illustrates four rows of circumferentially disposed pores 14d, as will be understood by a person having ordinary skill in the art, pores 14d may include less or more than four rows of circumferentially disposed pores. Moreover, pores 14e may include multiple pores arranged laterally along the length of at least the distal region of the expandable conduit. As shown in FIG. 16C, pores 14e may be proximal to pores 14d. As will be understood by a person having ordinary skill in the art, the plurality of pores described herein may have any combination of the arrangements and configurations described above. For example, the laterally disposed pores may have a circular shape, and the circumferentially disposed pores may have a longitudinally extending shape, or any combination thereof.

Figure 17:
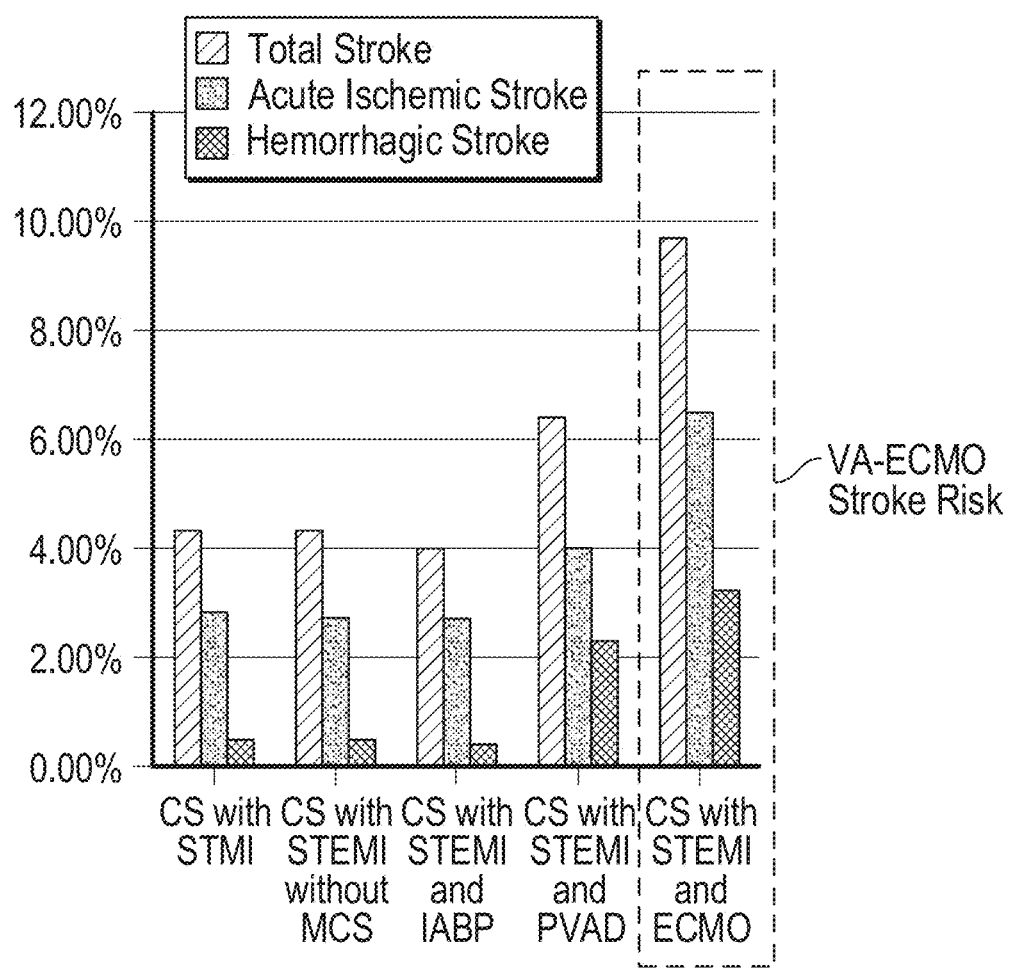
FIG. 17 is a graph illustrating VA-ECMO stroke risk.

FIG. 17 is a graph illustrating stroke risk for patient's undergoing various therapies include VA-ECMO. As shown, a patient undergoing VA-ECMO generally has the highest risk of total stroke, e.g., acute ischemic stroke and hemorrhagic stroke. In accordance with the principles of the present invention, the systems and methods described herein are expected to provide oxygenated blood to the cerebral vasculature and provide antegrade flow from the outlet of the self-expanding conduit. This in turn is expected to reduce the risk of ischemic stroke and reduce blood flow rates and pressures that could induce kidney injury.

Figure 18:
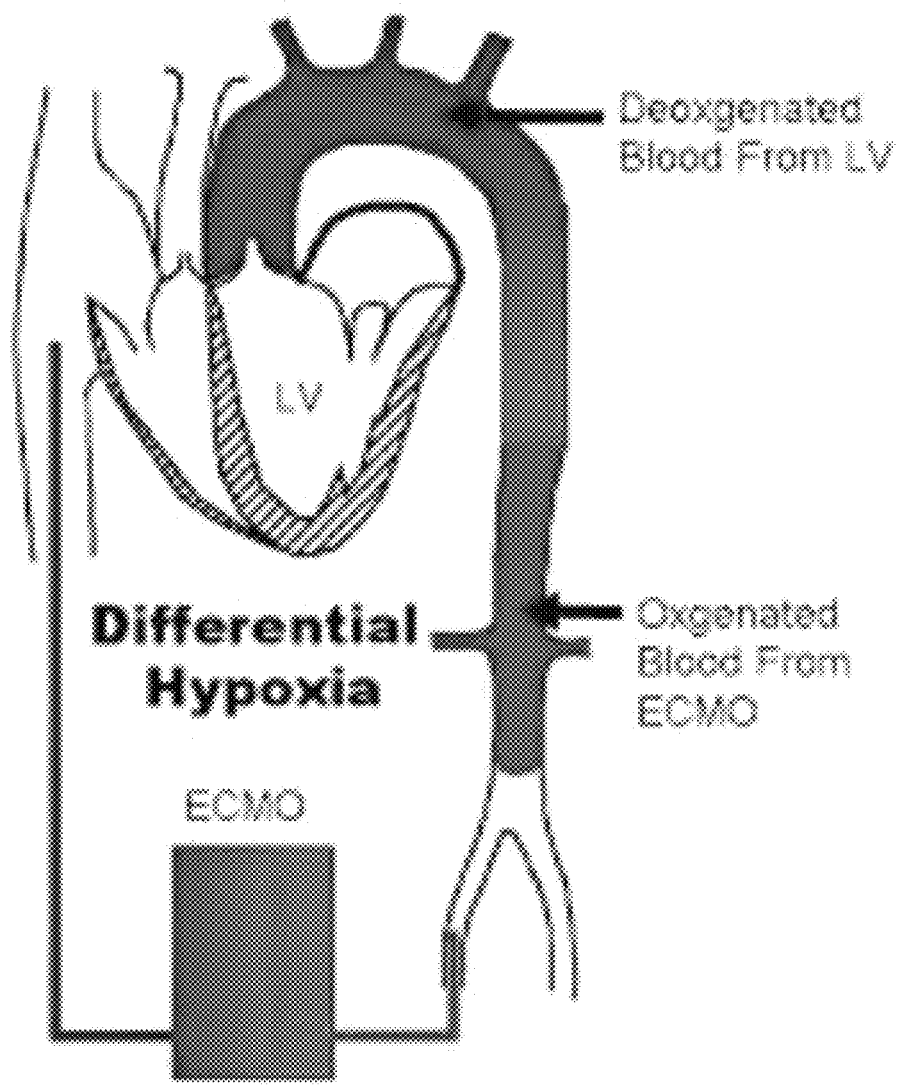
FIG. 18 depicts north-south syndrome in a patient on ECMO.

With respect to FIG. 18, a further expected benefit of the system and method of the present invention is described. FIG. 18 illustrates a situation referred to as "north-south syndrome" that may arise in a patient on ECMO, particularly patients having compromised lung function. In such cases, although the heat is beating, the blood returned to circulation by the left ventricle may be poorly oxygenated. In this case, if a conventional ECMO return catheter is employed, oxygenated blood reperfused into the patient mixes with the antegrade flow of deoxygenated blood from the lungs, resulting in differential hypoxia. Because the extension cannula of the present invention is designed to deliver blood into the ascending aorta, the system and methods of the present invention are expected to significantly ameliorate the effect of compromised lung function and reduce the occurrence and severity of north-south syndrome.

Figure 19:
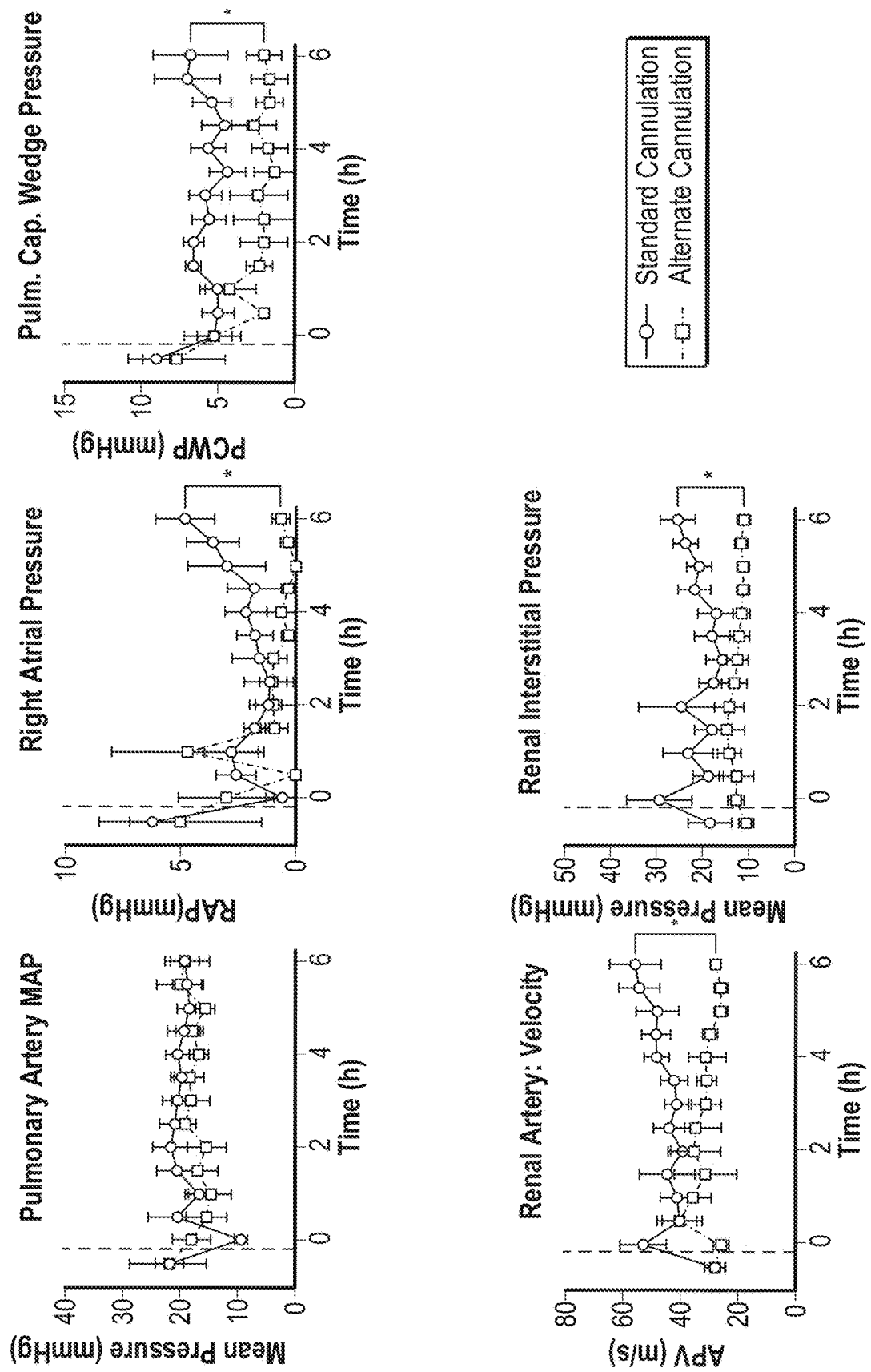
FIG. 19 is a series of graphs illustrating various parameters for standard conventional ECMO cannulation compared to those achieved using alternate cannulation (delivery of blood to the thoracic aorta) in accordance with the principles of the present invention.
Figure 20:
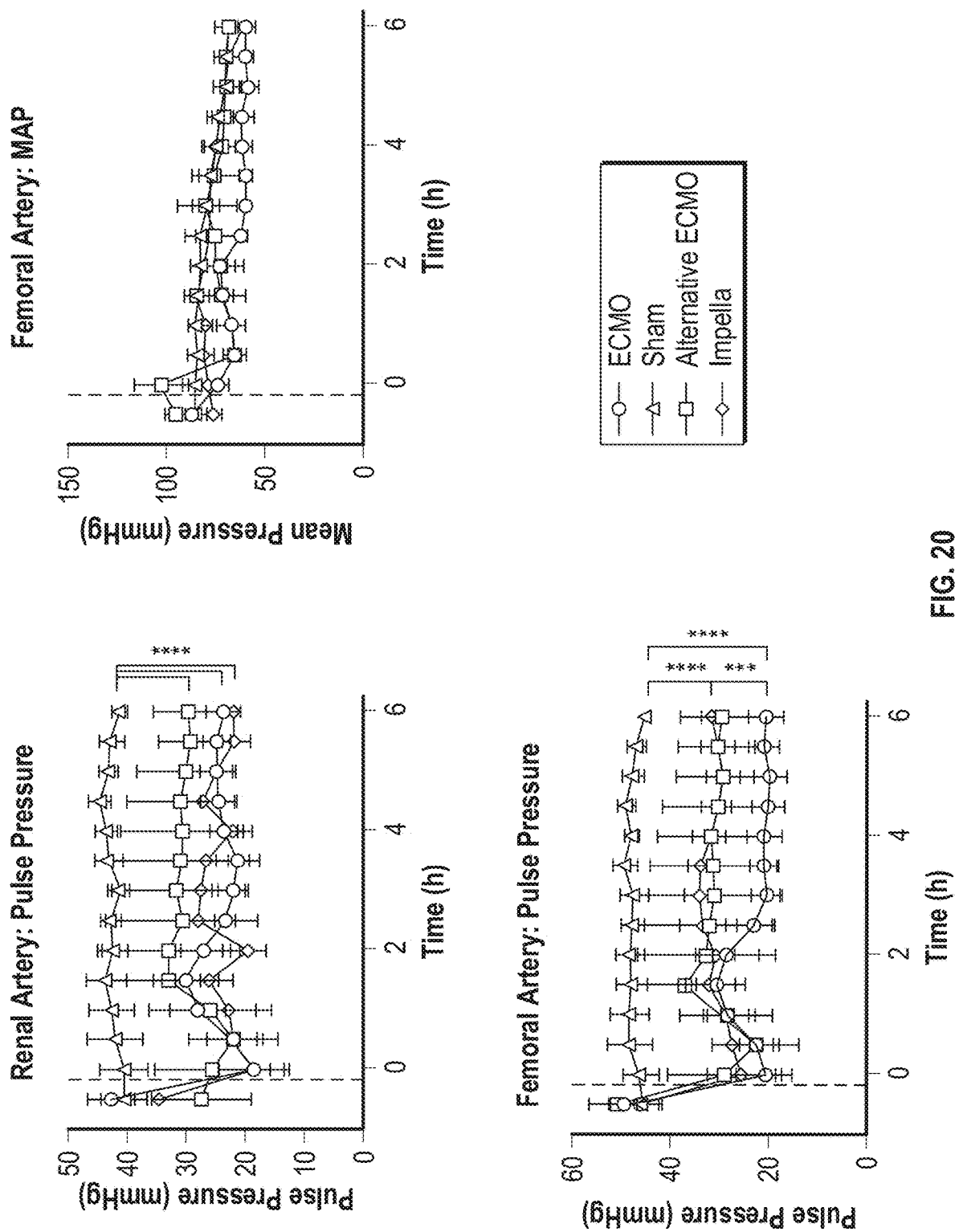
FIG. 20 is a series of graphs illustrating various parameters resulting from use of standard conventional ECMO cannulation, an Impella pump, and an exemplary system of the present invention.

Preclinical data from experiments utilizing an extension cannula constructed in accordance with the principles of the present invention demonstrate superior performance compared to conventional ECMO return cannulas. FIG. 19 is a series of graphs comparing various parameters measured during standard VA-ECMO cannulation and with use of the extension cannula of the present invention (defined as "Alternate Cannulation" in FIG. 19). In particular, the alternate cannulation of the present invention results in reduced pulmonary artery mean arterial pressure (MAP), reduced right arterial pressure, reduced pulmonary capillary wedge pressure, reduced renal arterial flow velocity, and reduced renal interstitial pressure (organ pressure), compared to standard VA-ECMO cannulation. These findings suggest that placement of an extension cannula may reduce cardiac, lung, and kidney injury when compared to standard VA-ECMO alone. Specifically, this data shows reduced heart pressures (right atrial pressure and pulmonary capillary wedge pressure), normal renal artery velocity, and normal renal interstitial (organ) pressures with alternate cannulation as opposed to standard cannulation (delivery of blood to the femoral artery). Further, as shown in FIG. 20, the alternate cannulation of the present invention provides increased pulsatile arterial flow in the renal artery and the femoral artery compared to standard VA-ECMO cannulation. Compared to sham operated animals, standard femoral cannulation ECMO reduces renal and femoral artery pulse pressure, e.g., pulsatility. Compared to standard cannulation, alternative cannulation (delivery of blood to the thoracic aorta) has increased renal and femoral artery pulse pressure, e.g., pulsatility. Improved physiologic pulsatility is further associated with less injury.

Figure 21:
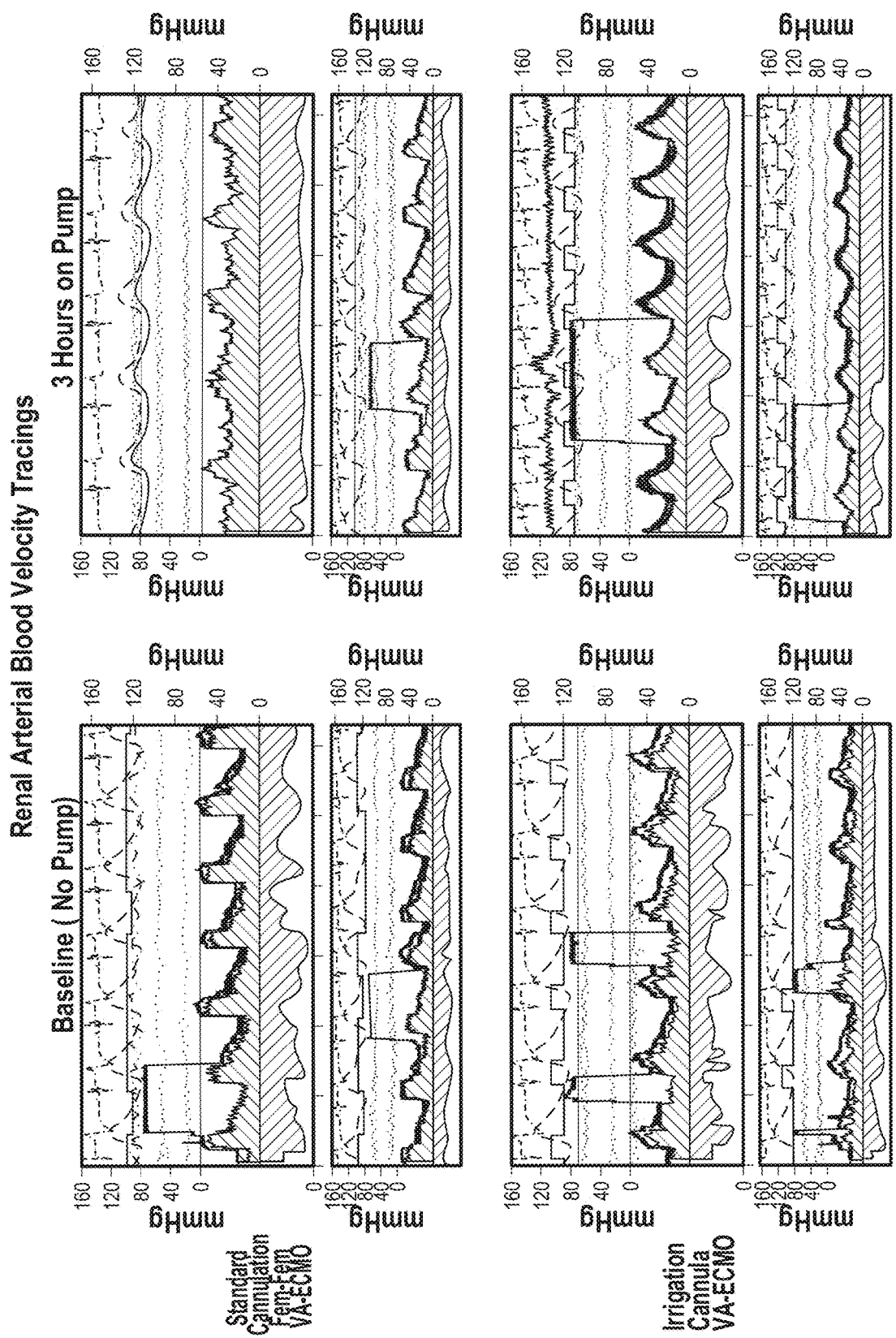
FIG. 21 is a series of graphs representing renal arterial blood velocity obtained for standard conventional ECMO cannulation and an exemplary alternate (irrigation) cannulation system of the present invention.
Figure 23:
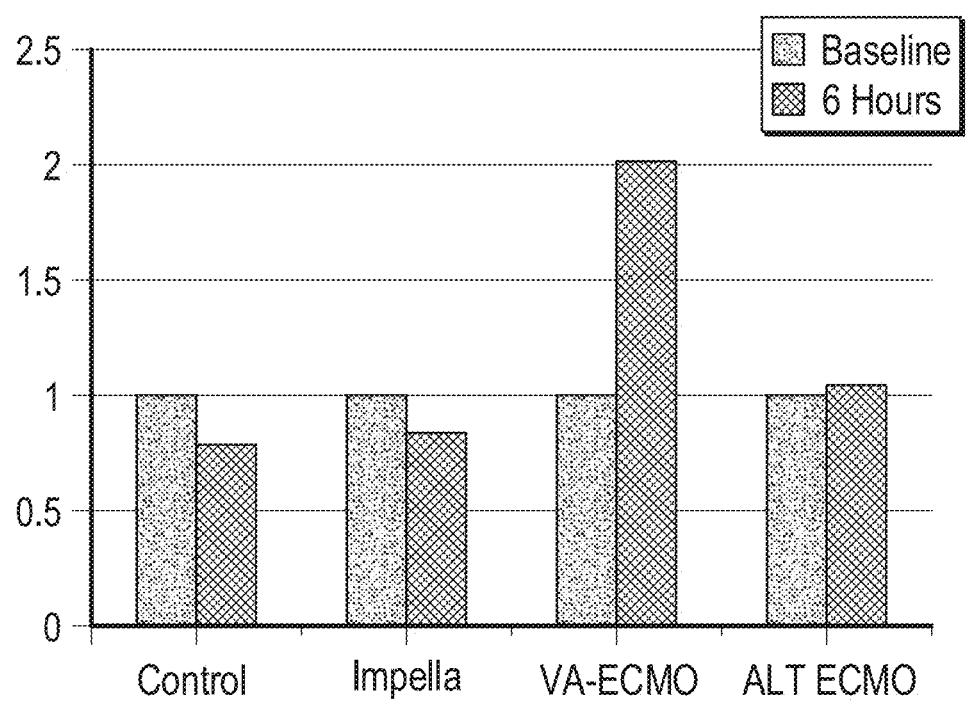
FIG. 23 is a graph showing urinary levels of kidney injury molecules associated with use of standard conventional ECMO cannulation and an exemplary alternate cannulation system of the present invention.

FIGS. 21 and 22 provide further comparisons of use of the alternate cannulation of the present invention compared to standard ECMO cannulation, demonstrating improved renal arty pulsatility and reduced microvascular resistance in the kidney. Regarding FIG. 21, compared to standard cannulation, alternate (irrigation) cannulation preserves pulsatility in the renal artery after three hours of pumping. Regarding FIG. 22, compared to standard cannulation, alternate (irrigation) cannulation preserves pulsatility (renal resistance index) and reduces renal arterial microvascular resistance in the renal artery after two and six hours of pumping. Similarly, FIG. 23 demonstrates that the alternate cannulation of the present invention ("ALT ECMO") results in lower levels of kidney injury molecule 1 (KIM-1) in the urine, indicating less kidney injury suffered by the patient. Compared to standard VA-ECMO, ALT ECMO is associated with lower (normal) levels of kidney injury marker in the urine.

Figure 24A:
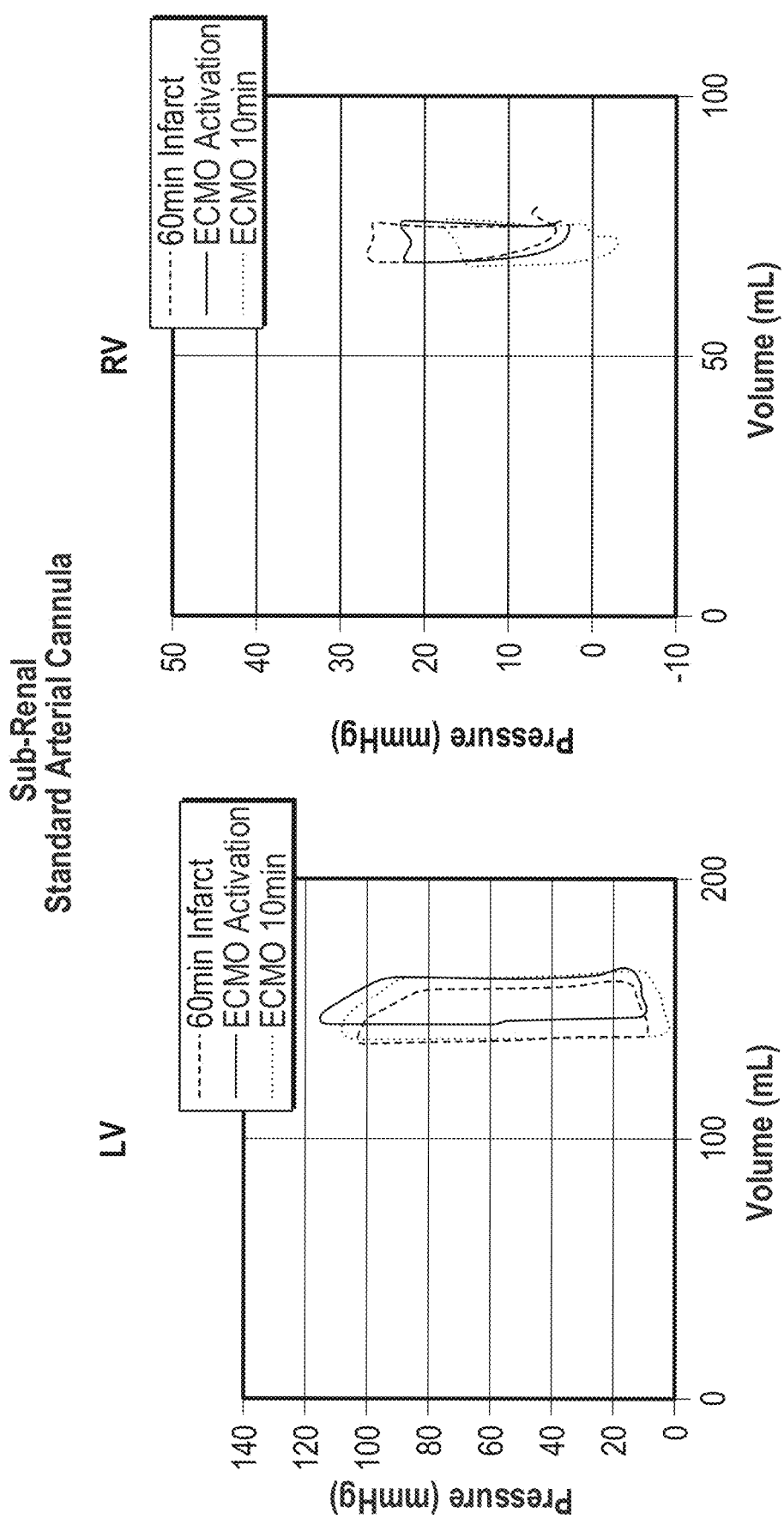
FIG. 24A illustrates left ventricular and right ventricular response during conventional ECMO cannulation.
Figure 24B:
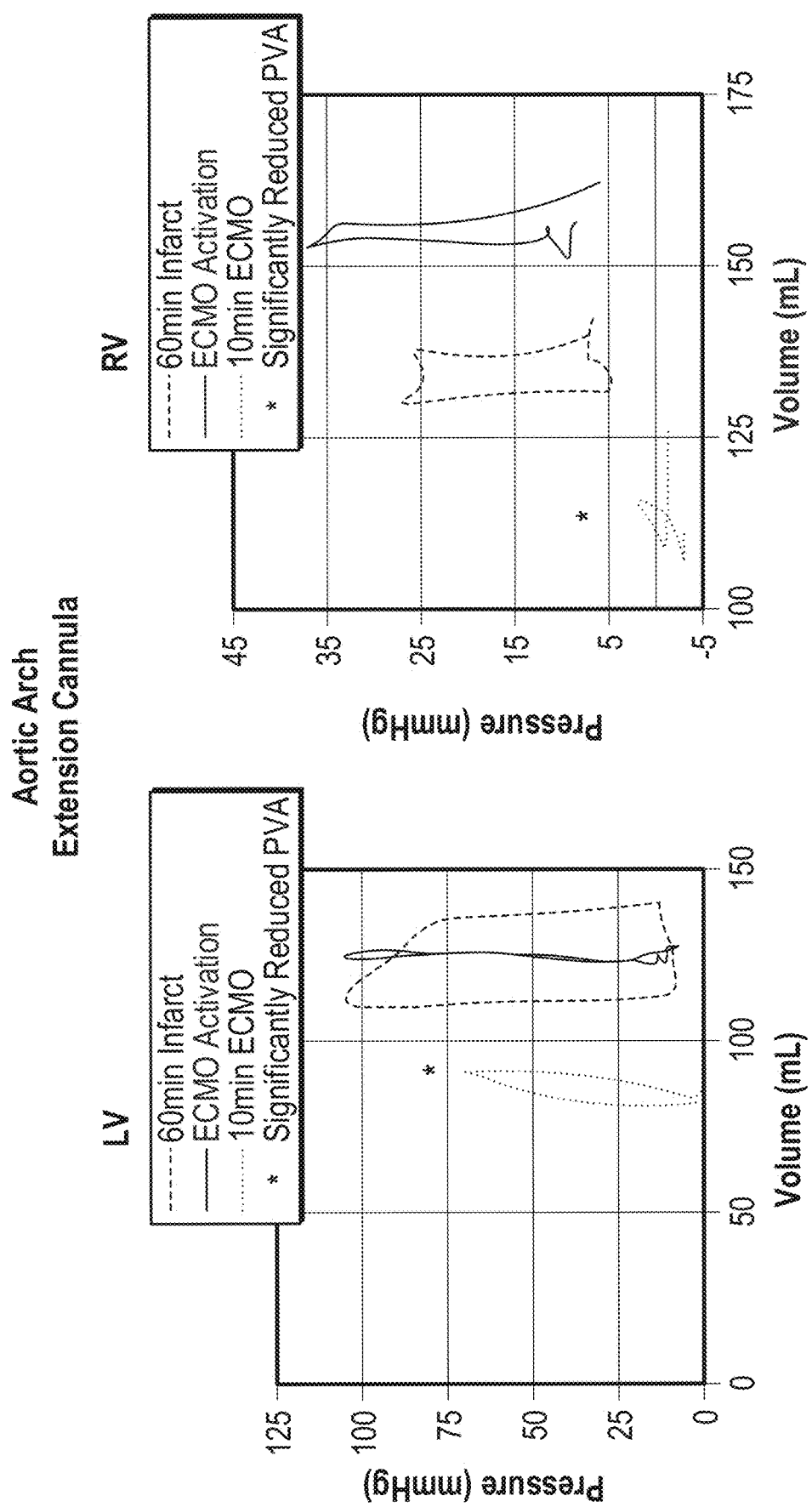
FIG. 24B illustrates left ventricular and right ventricular response during ECMO using the extension cannula of the present invention.

FIGS. 24A and 24B provide a further comparison of use of the alternate cannulation of the present invention compared to standard ECMO cannulation, demonstrating significant and unexpected reduction in both left and right ventricular workload. FIG. 24A is a graph of measured Pressure versus Volume that includes traces for the left and right ventricles at 60-minutes post-infarct, immediately after commencement of arterial ECMO cannulation within the femoral artery at a standard sub-renal outlet location, and after ten minutes of standard arterial ECMO cannulation. The area within the respective Pressure versus Volume loops, referred to as "PVA", is a measure of the work performed by the heart during the cardiac cycle. The graphs of FIG. 24A show that the pressure/volume loops for the left ventricle (LV) are substantially unchanged by ECMO reperfusion. Similarly, the right ventricle (RV) also does not experience a significant reduction in workload after standard arterial ECMO cannulation. By way of possible explanation, but without intending to be limiting, it is postulated that the left and right ventricular workload is substantially unchanged because introduction of continuous high flow below the renal arteries causes the blood column in the descending aorta to stagnate, which in turn causes the LV pressures to remain high. Thus, it is believed that the heart must continue working to overcome the resistance to antegrade flow created by the ECMO-infused blood. Accordingly, during standard ECMO cannulation, femoral delivery of arterial blood pressurizes the entire aorta, thereby increasing the load against which the native heart must pump.

In contrast, as shown in FIG. 24B, when the extension cannula of the present invention is deployed to extend the ECMO outlet within the aortic arch, both the left ventricle (LV) and the right ventricle (RV) experience a significant reduction in workload after commencement of ECMO activation, and thereafter, compared to standard arterial ECMO cannulation in FIG. 24A. Specifically, the pressure/volume loops for the left ventricle (LV) significantly decrease, and the pressure/volume loops for the right ventricle (RV) decreases even more, thus illustrating the effectiveness of the extension cannula of the present invention in reducing cardiac workload during ECMO reperfusion. Again by way of explanation, but without intending to be limiting, it is postulated that the significant decrease in left and right ventricular workload is due to the delivery of blood into the aortic arch, which enhances antegrade blood flow to the descending aorta as well as the arteries adjoining the aortic arch. Thus, the resulting forward flow, which fully develops during the 10 minutes after commencement of ECMO reperfusion, unloads the LV, thereby causing lesser cardiac output, but at much lower pressure. Moreover, it is believed that the reduced load in the LV may assist blood transiting the lungs, further reducing RV workload. Accordingly, by delivering blood in the aortic arch, the arterial tree is not pressurized, thereby avoiding increased pressure load that the heart might otherwise have to work against, which allows for more effective venous drainage of the heart, and thus reduced RV and LV volumes, without the cost of increasing ventricular pressure.

Figure 25:
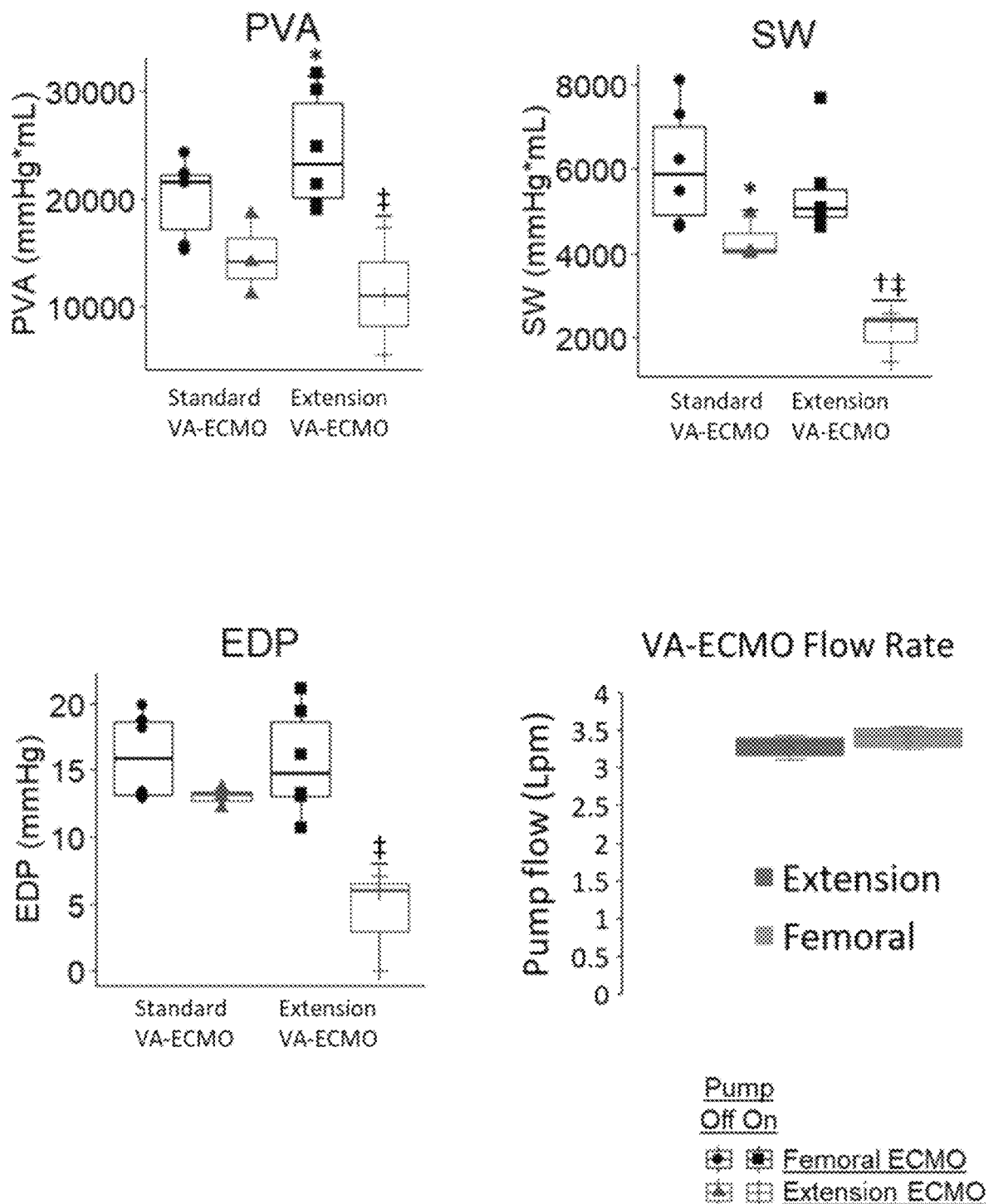
FIG. 25 are graphs illustrating pressure volume area (PVA), stroke work (SW), and end-diastolic pressure (EDP) associated with use of standard conventional ECMO cannulation and an exemplary alternate cannulation system of the present invention.

FIG. 25 are graphs illustrating pressure volume area (PVA), stroke work (SW), and end-diastolic pressure (EDP) associated with use of standard conventional VA-ECMO cannulation and the alternate extension cannulation of the present invention. As shown in FIG. 25, despite equivalent rates of flow through the VA-ECMO circuits (bottom right), compared with standard conventional VA-ECMO, use of the alternate extension cannulation of the present invention reduces PVA, SW, and EDP, thereby evidencing that the alternate extension cannulation of the present invention reduces cardiac workflow.

Figure 26B:
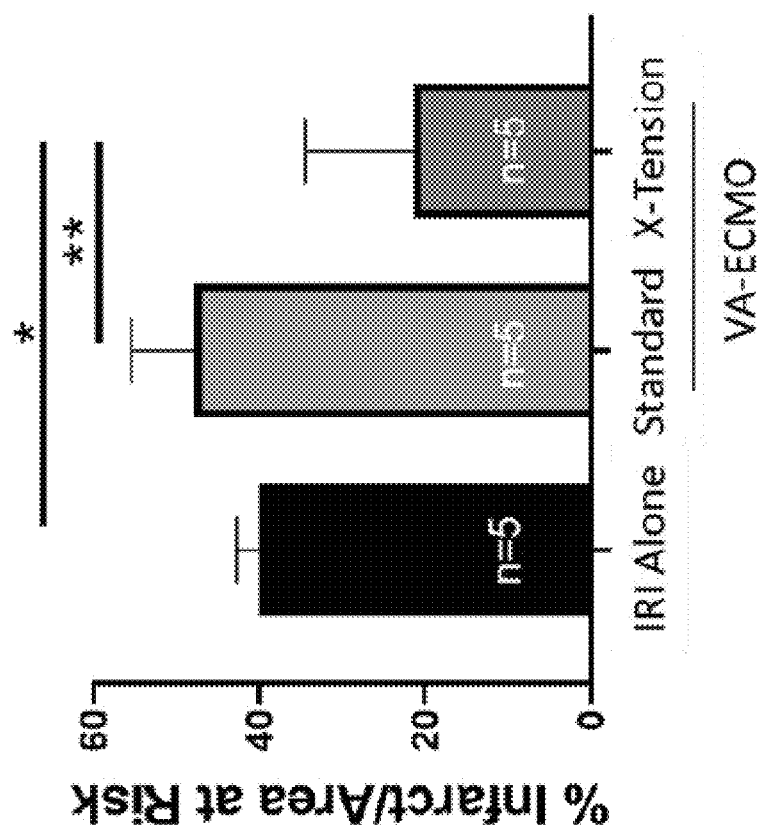
FIG. 26B is a graph show infarct size associated with standard ischemia and reperfusion injury (IRI) and use of standard conventional ECMO cannulation and an exemplary alternate cannulation system of the present invention.
Figure 26A:
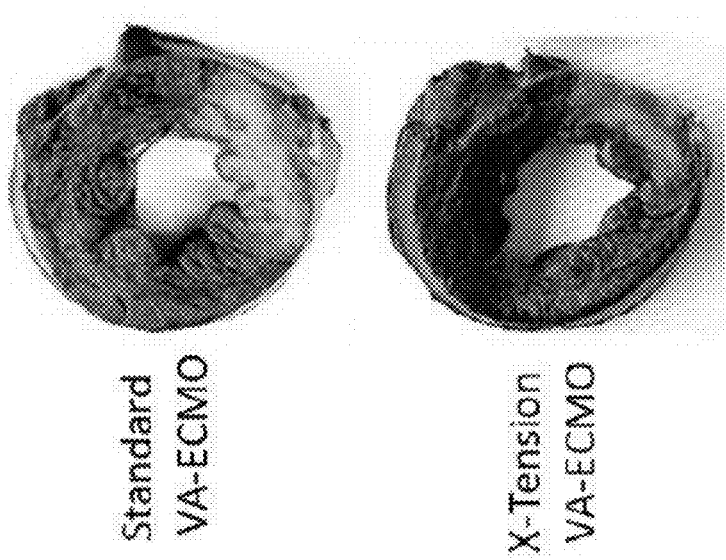
FIG. 26A illustrates infarct size associated with use of standard conventional ECMO cannulation and an exemplary alternate cannulation system of the present invention.

FIG. 26A illustrates infarct size associated with use of standard conventional ECMO cannulation and the alternate cannulation of the present invention. As shown in FIG. 26B, infarct size associated with use of the alternate extension cannulation of the present invention is much lower than the infarct sizes associated with standard ischemia and reperfusion injury (IRI) and with use of standard conventional ECMO cannulation.

Figure 27:
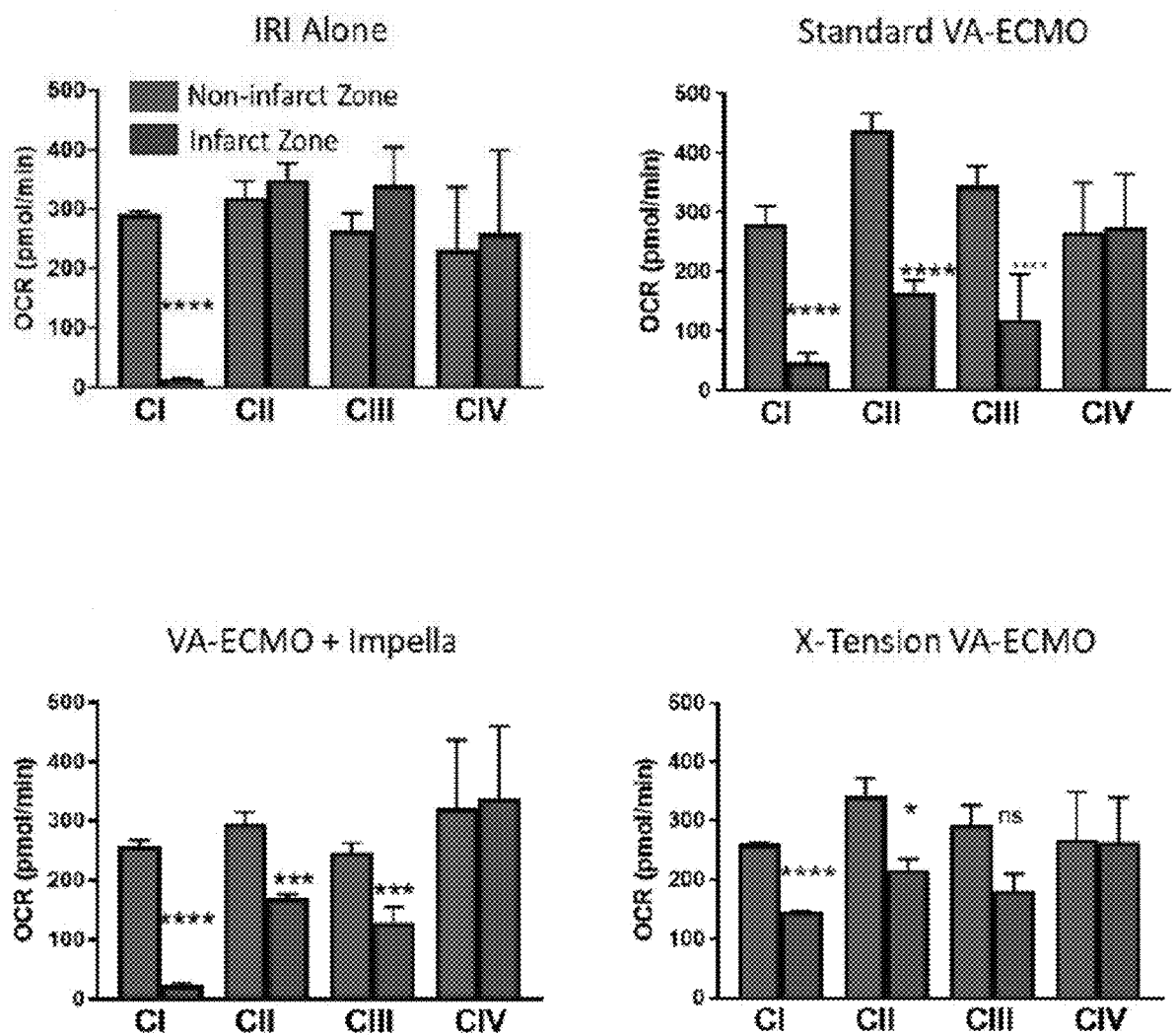
FIG. 27 are graphs illustrating oxygen consumption rate (OCR) associated with standard ischemia and reperfusion injury (IRI) and use of standard conventional ECMO cannulation, with and without an Impella, and an exemplary alternate cannulation system of the present invention.

FIG. 27 are graphs illustrating oxygen consumption rate (OCR) associated with standard ischemia and reperfusion injury (IRI) and use of standard conventional ECMO cannulation, with and without an Impella device, and the alternate extension cannulation of the present invention, which is indicative of the function of the mitochondria. Mitochondria are known as the "powerhouse" of the cell, generating ATP via oxidative phosphorylation (OXPHOS) complexes, which are present in the inner membrane of mitochondria. These complexes are known as NADH: ubiquinone oxidoreductase (complex I), succinate dehydrogenase (complex II), ubiquinol—cytochrome c oxidoreductase (complex III, or cytochrome $bc_1$ complex), cytochrome c oxidase (complex IV), and ATP synthase (complex V).

Complex I (CI) is the largest and most complicated component of the respiratory chain. Using the bovine heart as the model system, previous work has characterized all the complex I subunits and cloned the encoding genes. Mitochondrial CI accounts for 40% of proton motive force required to maintain ATP synthase in the electron transport chain (ETC). In a recent study, it was shown that reducing left heart workload with a mechanical pump can reduce myocardial damage and preserve mitochondrial CI function. See, e.g., Lija Swain, PhD, et al., Transvalvular Ventricular Unloading before Reperfusion in Acute Myocardial Infarction, Journal of the American College of Cardiology, Vol. 76, No. 6, 2020. The study further found that use of VA-ECMO during a heart attack fails to reduce left heart workload and increases myocardial damage, and significantly reduces mitochondrial CI function. This effect of VA-ECMO cannot be rescued by placing an unloading pump after VA-ECMO has been initiated. The study illustrated that using the alternate extension cannulation of the present invention with VA-ECMO reduces left heart workload, reduces myocardial damage, and improves function of mitochondrial CI.

Figure 28:
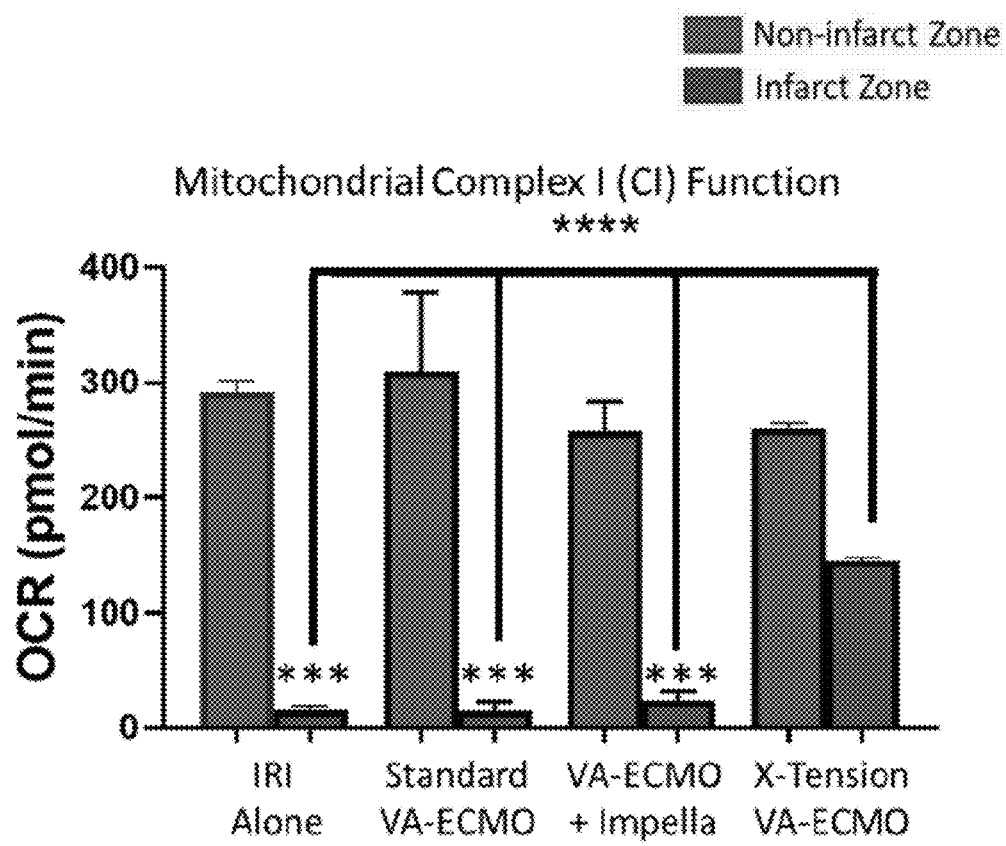
FIG. 28 is a graph illustrating oxygen consumption rate (OCR) associated with standard ischemia and reperfusion injury (IRI) and use of standard conventional ECMO cannulation, with and without an Impella, and an exemplary alternate cannulation system of the present invention for mitochondrial complex I (CI) function.

For example, as shown in FIG. 27, compared with IRI alone, standard conventional VA-ECMO alone, and standard conventional VA-ECMO with an Impella device, use of the alternate extension cannulation of the present invention with VA-ECMO preserves function of mitochondrial CI, as measured by oxygen consumption rate (OCR), which when impaired, contributes to myocardial damage and infarct size. Moreover, as shown in FIG. 28, compared to the non-infarct zone, mitochondrial CI function is significantly reduced in the infarct zone after IRI alone, standard conventional VA-ECMO alone, and standard conventional VA-ECMO with an Impella device. In contrast, mitochondrial CI function is significantly higher in the infarct zone after treatment using the alternate extension cannulation of the present invention with VA-ECMO. These data identify for the first time that the point of delivery for arterial blood returning from VA-ECMO promotes a cardio-protective effect on the heart, which has implications for any patient receiving VA-ECMO and especially for patients receiving VA-ECMO who are having a heart attack or heart injury.

While various illustrative embodiments of the invention are described above, it will be apparent to one skilled in the art that various changes and modifications may be made therein without departing from the invention. For example, as will be understood by a person having ordinary skill in the art, the systems and methods described herein are not limited for use with a VA-ECMO system. For example, the inventive extension cannula may also be used with, e.g., a venous-venous ECMO (VV-ECMO) system. Moreover, the extension cannulas and in-line connectors described herein may be used in conjunction with a conventional ECMO drainage catheter such that the extension cannula extends from the drainage catheter at the femoral vein to within the pulmonary artery or right ventricle of the patient, thereby permitting blood to be pumped directly out of the heart, effectively functioning as a ventricular assist device.

Figure 29A:
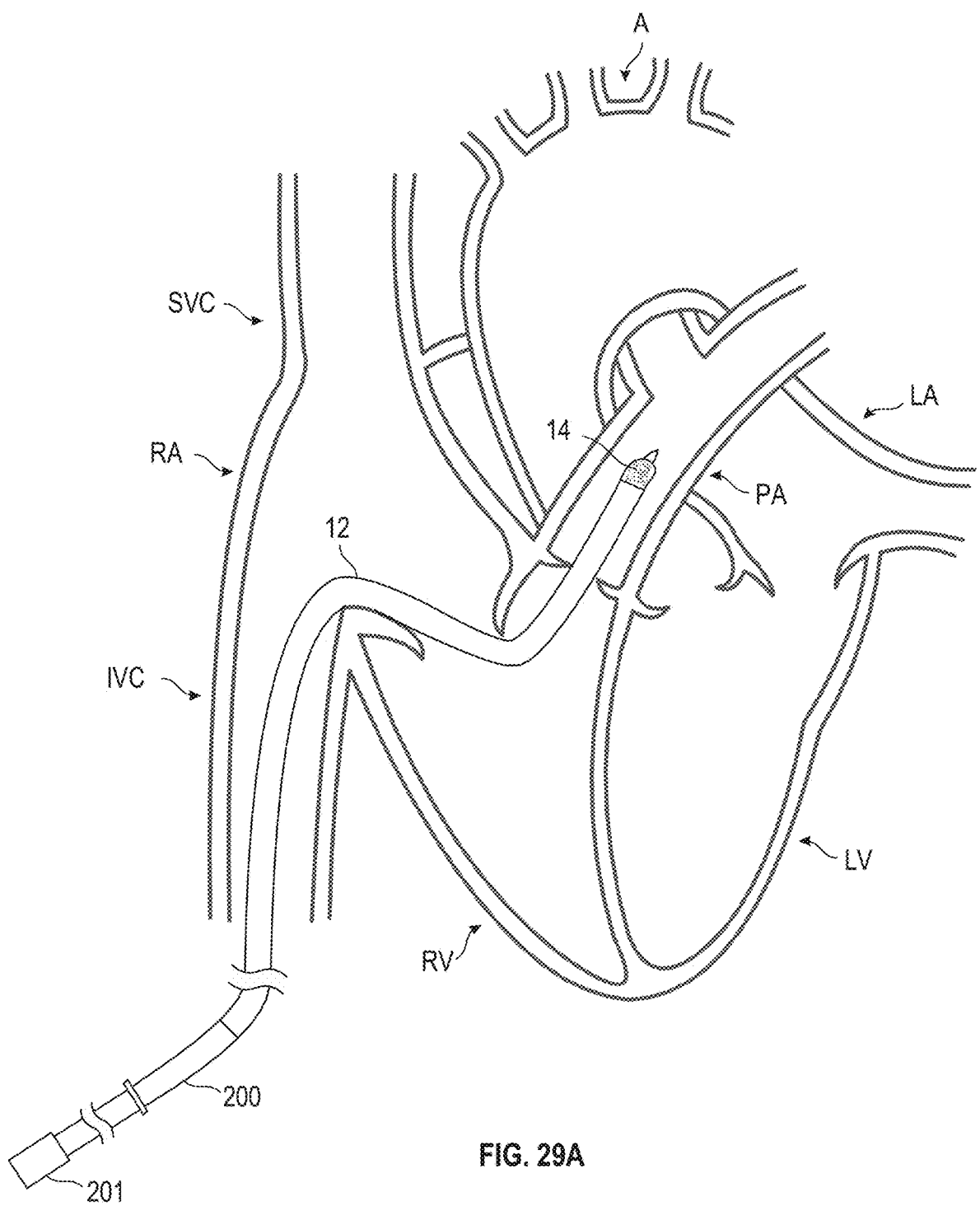
FIG. 29A illustrates an extension cannula in an ECMO system constructed in accordance with the principles of the present invention, where a distal end of the extension cannula is disposed within the pulmonary artery and a proximal end of the extension cannula is coupled to a conventional ECMO cannula via the femoral vein.
Figure 29B:
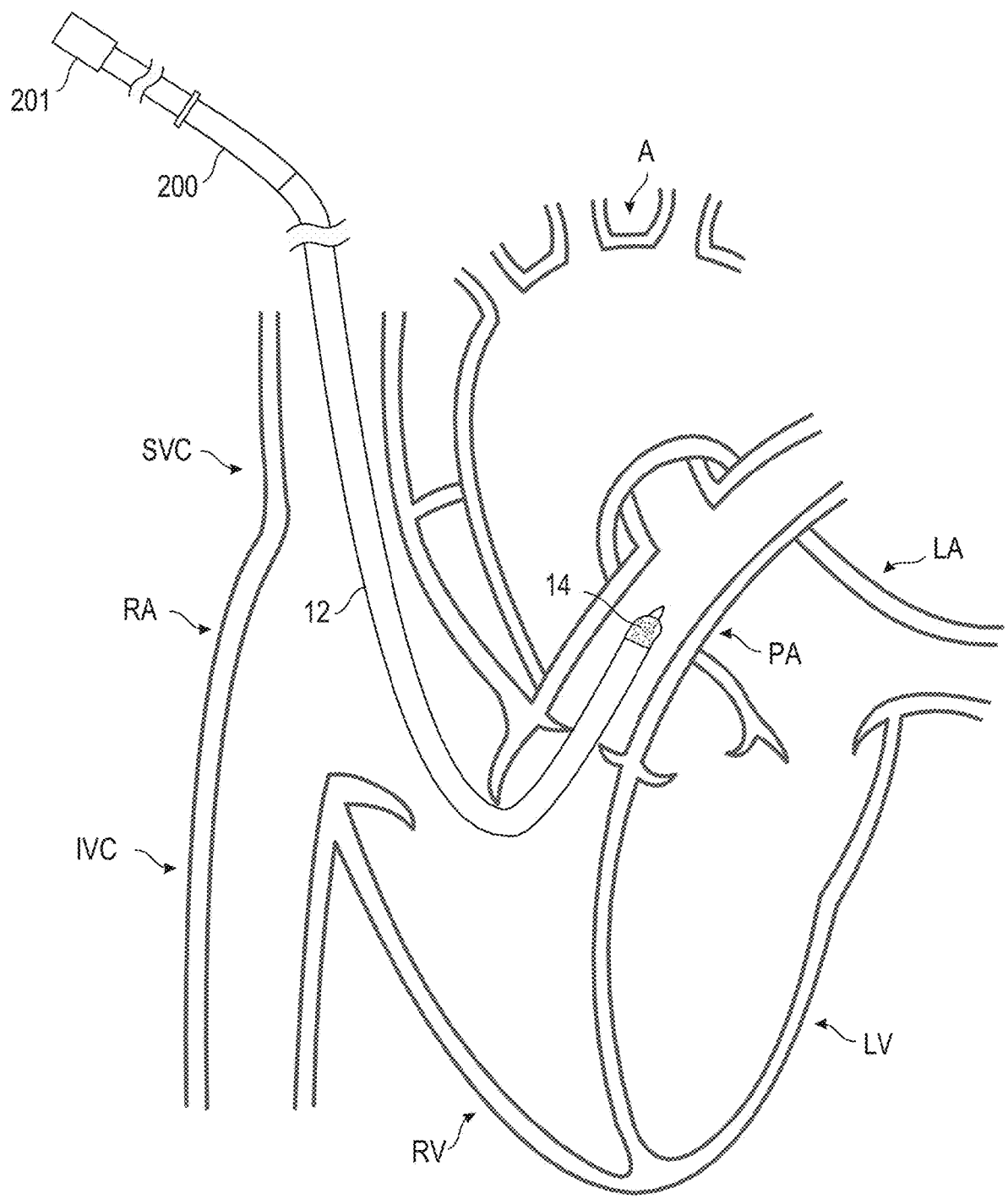
FIG. 29B illustrates an extension cannula in an ECMO system constructed in accordance with the principles of the present invention, where a distal end of the extension cannula is disposed within the pulmonary artery and a proximal end of the extension cannula is coupled to a conventional ECMO cannula via the internal jugular vein.

As shown in FIGS. 29A and 29B, any of the extension cannulas described herein, e.g., extension cannula 10, 10', 10'', 10''', 90, 90', 100, 100', may be used in conjunction with conventional ECMO drainage catheter 200 in fluid communication with ECMO drainage machine 201, such that the pores of the expandable conduit, e.g., pores 14 of expandable conduit 12, are disposed within the pulmonary artery PA. For example, as shown in FIG. 29A, the extension cannula may be inserted via a femoral vein approach and have a length such that expandable conduit 12 extends through the femoral vein, inferior vena cava IVC, right atrium RA, and right ventricle RV, and pores 14 are disposed within pulmonary artery PA. Accordingly, the extension cannula may provide right heart support by draining blood from or delivering blood to the pulmonary artery PA via pores 14 through expandable conduit 12. In some embodiments, the extension cannula may have a length such that pores 14 are disposed within right ventricle RV, to thereby drain blood from or deliver blood to the right ventricle RV. Alternatively, the extension cannula may have a length such that the distal end of the extension cannula is disposed within pulmonary artery PA, and pores 14 are arranged at the distal region of the extension cannula such that pores 14 are disposed within both pulmonary artery PA and right ventricle RV, to thereby drain blood from or deliver blood to both pulmonary artery PA and right ventricle RV.

Alternatively, as shown in FIG. 29B, the extension cannula may be inserted via an internal jugular vein approach and have a length such that expandable conduit 12 extends through the internal jugular vein, superior vena cava SVC, right atrium RA, and right ventricle RV, and pores 14 are disposed within pulmonary artery PA. Accordingly, the extension cannula may provide right heart support by draining blood from or delivering blood to the pulmonary artery PA via pores 14 through expandable conduit 12. In some embodiments, the extension cannula may have a length such that pores 14 are disposed within right ventricle RV, to thereby drain blood from or deliver blood to the right ventricle RV. Alternatively, the extension cannula may have a length such that the distal end of the extension cannula is disposed within pulmonary artery PA, and pores 14 are arranged at the distal region of the extension cannula such that pores 14 are disposed within both pulmonary artery PA and right ventricle RV, to thereby drain blood from or deliver blood to both pulmonary artery PA and right ventricle RV. As will be understood by a person having ordinary skill in the art, the extension cannulas described above for use with a conventional ECMO cannula for delivering oxygenated blood directly to a location above the patient's renal veins, also may have a length such that the distal end region of the extension cannula, and accordingly the pores of the expandable conduit, are disposed within the pulmonary artery and/or the right ventricle, such that oxygenated blood may be delivered directly to the pulmonary artery and/or the right ventricle, respectively.

The appended claims are intended to cover all such changes and modifications that fall within the true scope of the invention.

What is claimed:

1. A kit for use with an ECMO machine, the kit comprising:
   a cannula comprising a proximal region having an inlet configured to be coupled to the ECMO machine, and an outlet configured to be disposed at a location within a patient's vasculature proximal of a patient's renal vessels;
   an extension cannula comprising:
      a flexible conduit having a proximal end, a distal end, a length extending therebetween, and a lumen in an expanded deployed state, the flexible conduit configured to transition from a collapsed insertion state to the expanded deployed state when in communication with a blood flow from the ECMO machine so that the lumen forms a continuation of a blood flow path through the cannula; and
      an elongated shaft having a distal region coupled to the distal end of the flexible conduit, the elongated shaft configured to advance the flexible conduit in the collapsed insertion state to locate the distal end beyond the patient's renal vessels; and
   a peel-away introducer disposed on at least a portion of the flexible conduit, the peel-away introducer configured to be retracted proximally relative to the flexible conduit and peeled off of the flexible conduit,
   wherein the length of the flexible conduit is selected so that when the proximal end is located within the outlet at the location within the patient's vasculature proximal of the patient's renal vessels, the distal end extends beyond the patient's renal vessels, and
   wherein the elongated shaft is configured so that the blood flow path does not pass through the elongated shaft.

2. The kit of claim 1, wherein the peel-away introducer comprises a diameter that is at most equal to a diameter of the cannula.

3. The kit of claim 1, wherein the peel-away introducer is configured to extend along an entire length of the flexible conduit.

4. The kit of claim 1, wherein the elongated shaft extends from the distal end of the flexible conduit proximally along a lateral side of the flexible conduit.

5. The kit of claim 1, wherein the elongated shaft extends from the distal end of the flexible conduit proximally within the lumen along a longitudinal axis of the flexible conduit.

6. The kit of claim 5, wherein the elongated shaft extends along a center portion of the lumen.

7. The kit of claim 1, wherein the elongated shaft comprises a hypotube having a lumen configured to receive a guidewire therethrough.

8. The kit of claim 1, wherein the extension cannula further comprises a support coupled to a distal region of the flexible conduit, the support extending circumferentially along the flexible conduit and configured to transition from a collapsed delivery state to an expanded deployed state.

9. The kit of claim 8, wherein the extension cannula further comprises a plurality of connection structures extending between the distal end of the flexible conduit and the support, the plurality of connection structures configured to transition from a collapsed delivery state to an expanded deployed state.

10. The kit of claim 9, wherein a distal end of the elongated shaft comprises an atraumatic tip configured to be coupled to the support via the plurality of connection structures.

11. The kit of claim 1, wherein the flexible conduit comprises at least one of polyethylene, polyurethane, or nylon.

12. The kit of claim 1, wherein an outlet of the flexible conduit comprises one or more pores disposed at a distal region of the flexible conduit.

13. The kit of claim 1, wherein the proximal end of the flexible conduit is configured to be fixedly coupled to the cannula within the outlet of the cannula.

14. The kit of claim 1, further comprising one or more sensors disposed at a distal region of the extension cannula, the one or more sensors configured to measure at least one of pressure, flow, or oxygen saturation within the patient's vasculature.

15. The kit of claim 14, further comprising:
a console operatively coupled to the one or more sensors, the console configured to display measurements of the one or more sensors,
wherein the elongated shaft comprises a lumen sized and shaped to receive one or more electrical wires extending between the one or more sensors and the console.

16. A method for improving systemic perfusion, the method comprising:
advancing a distal end of a flexible extension cannula within a patient's vasculature via an elongated shaft coupled to the distal end of the flexible extension cannula, a proximal region of the flexible extension cannula coupled to an outlet of an ECMO return cannula in fluid communication with an ECMO machine, at least a portion of the flexible extension cannula disposed within a peel-away introducer;
positioning the peel-away introducer into the patient's vasculature, such that a proximal end of the peel-away introducer remains external to the patient and the distal end of the flexible extension cannula is positioned within the patient's vasculature;
retracting the peel-away introducer relative to the flexible extension cannula and peeling the peel-away introducer off of the flexible extension cannula;
advancing the ECMO return cannula into the patient's vasculature such that the flexible extension cannula extends from a location proximal to the patient's renal vessels to a location beyond the patient's renal vessels;
transitioning the flexible extension cannula from a collapsed insertion state to an expanded deployed state when in communication with a blood flow from the ECMO machine, the flexible extension cannula comprising a lumen in the expanded state; and
delivering the blood flow through the lumen of the flexible extension cannula to the location beyond the patient's renal vessels via a plurality of pores disposed at a distal region of the flexible extension cannula to thereby improve systemic perfusion,
wherein the elongated shaft is configured so that the blood flow path does not pass through the elongated shaft.

17. The method of claim 16, wherein transitioning the flexible extension cannula from the collapsed insertion state to the expanded deployed state comprises transitioning a support extending circumferentially along a distal region of the flexible extension cannula from a collapsed delivery state to an expanded deployed state.

18. The method of claim 17, wherein transitioning the flexible extension cannula from the collapsed insertion state to the expanded deployed state comprises transitioning a plurality of connection structures extending from the distal end of the flexible extension cannula to the support from a collapsed delivery state to an expanded deployed state.

\* \* \* \* \*